US012173348B2

(12) United States Patent
Tabata et al.

(10) Patent No.: US 12,173,348 B2
(45) Date of Patent: Dec. 24, 2024

(54) METHOD FOR DETECTING ENZYMATIC REACTION PRODUCT

(71) Applicant: Japan Science and Technology Agency, Saitama (JP)

(72) Inventors: Kazuhito Tabata, Tokyo (JP); Yoshihiro Minagawa, Tokyo (JP); Hiroyuki Noji, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 1048 days.

(21) Appl. No.: 16/976,399

(22) PCT Filed: Mar. 4, 2019

(86) PCT No.: PCT/JP2019/008411
§ 371 (c)(1),
(2) Date: Aug. 27, 2020

(87) PCT Pub. No.: WO2019/168200
PCT Pub. Date: Sep. 6, 2019

(65) Prior Publication Data
US 2020/0407769 A1  Dec. 31, 2020

(30) Foreign Application Priority Data

Mar. 2, 2018  (JP) ................. 2018-037085

(51) Int. Cl.
*C12Q 1/34* (2006.01)
*C12Q 1/70* (2006.01)
(52) U.S. Cl.
CPC ............. *C12Q 1/34* (2013.01); *C12Q 1/70* (2013.01); *C12Y 302/01* (2013.01); *G01N 2333/924* (2013.01)
(58) Field of Classification Search
CPC .......... C12Q 1/34; C12Q 1/70; C12Y 302/01; G01N 2333/924; G01N 2333/11
See application file for complete search history.

(56) References Cited

U.S. PATENT DOCUMENTS

| | | | |
|---|---|---|---|
| 4,279,993 A | 7/1981 | Magers et al. |
| 4,716,222 A | 12/1987 | Wallenfels et al. |
| 5,837,520 A | 11/1998 | Shabram et al. |
| 5,900,360 A | 5/1999 | Welch et al. |
| 6,372,895 B1 | 4/2002 | Bentsen et al. |
| 2004/0086849 A1 | 5/2004 | Shimasaki et al. |
| 2005/0202518 A1 | 9/2005 | Vedrine et al. |
| 2008/0268514 A1 | 10/2008 | Muller et al. |
| 2011/0281754 A1 | 11/2011 | Fischer et al. |
| 2013/0345088 A1* | 12/2013 | Noji et al. |
| 2014/0272941 A1 | 9/2014 | Gunnerson et al. |
| 2014/0272942 A1* | 9/2014 | Weiss et al. |
| 2017/0176430 A1* | 6/2017 | Noji et al. |
| 2019/0194717 A1 | 6/2019 | Noji et al. |

FOREIGN PATENT DOCUMENTS

| | | |
|---|---|---|
| JP | S56076049 A | 6/1981 |
| JP | S60252464 A | 12/1985 |
| JP | H1075779 A | 3/1998 |
| JP | 2000509971 A | 8/2000 |
| JP | 2002506626 A | 3/2002 |
| JP | 2002508193 A | 3/2002 |
| JP | 2002541858 A | 12/2002 |
| JP | 2003506455 A | 2/2003 |
| JP | 2006500940 A | 1/2006 |
| JP | 2006271396 A | 10/2006 |
| JP | 2008275511 A | 11/2008 |
| JP | 2010524505 A | 7/2010 |
| JP | 2011139656 A | 7/2011 |
| JP | 2013101110 A | 5/2013 |
| JP | 2014514930 A | 6/2014 |
| JP | 201534809 A | 2/2015 |
| JP | 2018038384 A | 3/2018 |
| WO | 9931280 A1 | 6/1999 |
| WO | 9947539 A1 | 9/1999 |
| WO | 2012121310 A1 | 9/2012 |
| WO | WO 2016/006208 A1 * | 1/2016 |
| WO | 2018043733 A1 | 3/2018 |
| WO | 2018181488 A1 | 10/2018 |

OTHER PUBLICATIONS

Moriizumi et al. Osmolyte-enhanced protein synthesis activity of a reconstituted translation system. ACS Synthetic Biology, (2019), 8: 57-567. (Year: 2019).*
Japanese Office Action dated Jan. 10, 2023 issued in Japanese Patent Application No. 2020-503672 (with English language machine translation attached).
International Search Report and Written Opinion dated May 14, 2019 from PCT International Appln. No. PCT/JP2019/008411 (with English language translation of the International Search Report).
International Search Report dated Nov. 21, 2017 in connection with PCT International Application No. PCT/JP2017/031689 (with English language translation).
Rowland, B. et al., "Fluorescence-based detection of lacZ reporter gene expression in intact and viable bacteria including *Mycobacterium* species," FEMS Microbiology Letters, 1999, vol. 179, pp. 317-325.
Zhang, F. et al., "A simple and rapid fluorescent neuraminidase enzymatic assay on a microfluidic chip," Diagnostic Microbiology and Infectious Disease, 2012, vol. 74, pp. 263-266.

(Continued)

*Primary Examiner* — Iqbal H Chowdhury
(74) *Attorney, Agent, or Firm* — Amster, Rothstein & Ebenstein LLP

(57) ABSTRACT

Provided is a technique that can be used to detect a pathogenic microorganism such as influenza virus with high sensitivity, and specifically, a method for detecting a reaction product, including reacting an enzyme with a substance serving as a substrate for a reaction involving the enzyme in a hydrophilic solvent that is in interfacial contact with a hydrophobic solvent, wherein the reaction product is produced directly and released from the substrate, and wherein the hydrophilic solvent contains at least one of a buffering substance or trimethylamine oxide (TMAO).

15 Claims, 6 Drawing Sheets

(56) References Cited

OTHER PUBLICATIONS

Kim, S.H. et al., "Quantifying genetically inserted fluorescent protein in single iPS cells to monitor Nanog expression using electroactive microchamber arrays," Lab Chip, 2014, vol. 14, pp. 730-736.

Sakakihara S. et al., "A single-molecule enzymatic assay in a directly accessible femtoliter droplet array," Lab Chip, 2010, vol. 10, pp. 3355-3362.

Supplementary European Search Report dated Mar. 26, 2020 from European Patent Appln. No. EP 17846736.1.

Tabata et al., "Antibody-Free Digital Influenza Virus Counting Based on Neuraminidase Activity," Scientific Reports, vol. 9, No. 1, Article No. 1067, Jan. 31, 2019, 13 pages.

Vemula et al., "Current Approaches for Diagnosis of Influenza Virus Infections in Humans," Viruses, vol. 8, No. 4, Article No. 96, Apr. 12, 2016, 15 pages.

Office Action (Restriction Requirement) dated Jan. 29, 2020 from U.S. Appl. No. 16/329,829.

Non-Final Office Action dated Jul. 8, 2020 from U.S. Appl. No. 16/329,829.

Japanese Office Action dated Sep. 28, 2021 from Japanese Patent Application No. 2017-099579.

Kintses et al., "Picoliter Cell Lysate Assays in Microfluidic Droplet Compartments for Directed Enzyme Evolution," Chemistry and Biology, vol. 19, Issue 8, Aug. 24, 2012, pp. 1001-1009.

Chinese Office Action dated Dec. 15, 2021 from Chinese Patent Application No. 201780054148.5, with English language translation.

\* cited by examiner

A

B

METHOD FOR DETECTING ENZYMATIC REACTION PRODUCT

CROSS-REFERENCE TO RELATED APPLICATIONS

This application is a U.S. national stage entry under 35 U.S.C. § 371 of PCT International Patent Application No. PCT/JP2019/008411, filed Mar. 4, 2019, which claims priority to Japanese Patent Application No. 2018-037085, filed Mar. 2, 2018, the contents of each of which are hereby incorporated by reference in their entirety.

TECHNICAL FIELD

The present invention relates to a method for detecting an enzymatic reaction product. In particular, the present invention relates to a method for detecting a reaction product, including reacting an enzyme with a substance serving as a substrate for a reaction involving the enzyme in a hydrophilic solvent that is in interfacial contact with a hydrophobic solvent.

BACKGROUND ART

In recent years, a simple influenza virus test kit using immunochromatography has been developed (see Patent Literature 1). Since a method using immunochromatography can detect influenza virus for several minutes to several tens of minutes, the method is utilized for diagnosis, treatment or the like of infection.

Heretofore, a technique of optically detecting influenza virus based on a reaction between neuraminidase as an enzyme contained in influenza virus and a chromogenic substrate has been known (see Patent Literatures 2 and 3). Examples of the chromogenic substrate to be used include 4-methylumbelliferyl-N-acetyl-α-D-neuraminic acid (4 MU-NANA, see Patent Literature 2) and a derivative of 4-alkoxy-N-acetylneuraminic acid or 4,7-dialkoxy-N-acetylneuraminic acid (see Patent Document 3). For example, in the method using 4 MU-NANA as the chromogenic substrate, 4-methylumbelliferone, which is a fluorescent substance, is produced by the decomposition of 4 MU-NANA by neuraminidase. An enzymatic activity value of neuraminidase can be calculated based on the amount of 4-methylumbelliferone produced, and the number of particles of influenza virus can also be quantified based on the enzymatic activity value.

In the context of the present invention, Non-Patent Literature 1 discloses a method for carrying out a single-molecule enzyme assay by use of a femtoliter droplet array accessible directly from the outside, wherein the droplet is covered with oil.

CITATION LIST

Patent Literature

Patent Literature 1: Japanese Patent Laid-Open No. 2008-275511

Patent Literature 2: Japanese Patent Laid-Open No. 2011-139656

Patent Literature 3: National Publication of International Patent Application No. 2002-541858

Non-Patent Literature

Non-Patent Literature 1: S. Sakakihara et al., Lab Chip, 2010, 10, 3355-3362

SUMMARY OF INVENTION

Technical Problem

The method for detecting influenza virus based on immunochromatography is simple, but the method requires about $10^3$ to $10^4$ pfu/ml of virus for the detection, which disadvantageously has low detection sensitivity.

Then, it is a main object of the present invention to provide a technique that can be used to detect a pathogenic microorganism such as influenza virus with high sensitivity.

Solution to Problem

In order to solve the problem, the present invention provides the following [1] to [47].

[1] A method for detecting a reaction product, including reacting an enzyme with a substance serving as a substrate for a reaction involving the enzyme in a hydrophilic solvent that is in interfacial contact with a hydrophobic solvent, wherein the reaction product is produced directly and released from the substrate, and
   wherein the hydrophilic solvent contains at least one of a buffering substance or trimethylamine oxide (TMAO).

[2] A method for detecting a reaction product, including reacting an enzyme with a substance serving as a substrate for a reaction involving the enzyme in a hydrophilic solvent that is in interfacial contact with a hydrophobic solvent, the method including:
   a step of adding at least one of a buffering substance or trimethylamine oxide (TMAO) to the hydrophilic solvent to suppress migration of the reaction product to the hydrophobic solvent from the hydrophilic solvent.

[3] The method according to [1] or [2], wherein the concentrations of the buffering substance and trimethylamine oxide in the hydrophilic solvent are 1 M or more.

[4] The method according to any of [1] to [3], wherein the buffering substance is DEA (diethanolamine), HEPES (4-(2-hydroxyethyl)-1-piperazineethanesulfonic acid), sarcosine, or glycine.

[5] The method according to any of [1] to [4], wherein the hydrophilic solvent has a pH value greater than an acid dissociation constant (pKa) of the reaction product.

[6] The method according to [1] to [5],
   wherein:
   the hydrophilic solvent contains a pathogenic microorganism;
   the enzyme is an enzyme present on a surface of the pathogenic microorganism or in the pathogenic microorganism and having substrate cleavage activity;
   the substance is a chromogenic substrate; and
   the reaction product produced by cleavage of the chromogenic substrate involving the enzyme is optically detected.

[7] The method according to [6],
   wherein:
   the pathogenic microorganism is influenza virus;
   the enzyme is neuraminidase;
   the chromogenic substrate and the reaction product are 4-methylumbelliferyl-N-acetyl-α-D-neuraminic acid and 4-methylumbelliferone, respectively, or a derivative containing fluorescein and fluorescein, respectively.

[8] The method according to [6],
wherein:
the pathogenic microorganism is at least one selected from the group consisting of coronavirus, severe acute respiratory syndrome (SARS) coronavirus, middle east respiratory syndrome (MERS) virus, mumps virus, measles virus, nipah virus, canine distemper virus, human immunodeficiency virus (HIV), hepatitis B virus, human T cell leukemia virus (HTLV), Ebola virus, hepatitis C virus, Lassa virus, hantavirus, rabies virus, Japanese encephalitis virus, yellow fever virus, dengue virus, rubella virus, rotavirus, and norovirus; and
the enzyme is at least one selected from the group consisting of hemagglutinin-esterase, neuraminidase, reverse transcriptase, and RNA-dependent RNA polymerase.

[9] The method according to any of [1] to [6], wherein the substance is at least one selected from the group consisting of a derivative containing 4-methylumbelliferone, a derivative containing fluorescein, a derivative containing resorufin, and a derivative containing rhodamine.

[10] The method according to any of [6] to [9], wherein the hydrophilic solvent contains a biological sample separated from a subject infected with the pathogenic microorganism or a subject suspected to be infected with the pathogenic microorganism.

[11] A method for detecting a pathogenic microorganism in a biological sample separated from a subject infected with the pathogenic microorganism or a subject suspected to be infected with the pathogenic microorganism, the method including:
an introducing step of introducing a hydrophilic solvent that contains the biological sample and a substance serving as a substrate for a reaction involving an enzyme present on a surface of the pathogenic microorganism or in the pathogenic microorganism into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;
an enclosing step of introducing a hydrophobic solvent into the space to form in the receptacle a droplet of the hydrophilic solvent that is covered with the hydrophobic solvent and envelopes the pathogenic microorganism and the substance; and
a detecting step of optically detecting a reaction product produced by the reaction between the enzyme and the substance in the droplet,
wherein the hydrophilic solvent contains at least one of a buffering substance or trimethylamine oxide (TMAO).

[12] The method according to [11], wherein the concentrations of the buffering substance and trimethylamine oxide in the hydrophilic solvent are 1 M or more.

[13] The method according to [11] or [12], wherein the buffering substance is DEA (diethanolamine), HEPES (4-(2-hydroxyethyl)-1-piperazineethanesulfonic acid), sarcosine, or glycine.

[14] The method according to any of [11] to [13], wherein the hydrophilic solvent has a pH value greater than an acid dissociation constant (pKa) of the reaction product.

[15] The method according to any of [11] to [14], further including a step of determining the number and/or subspecies of the pathogenic microorganism based on detection intensity of the reaction product.

[16] The method according to any of [11] to [15],
wherein:
the pathogenic microorganism is influenza virus;
the enzyme is neuraminidase; and
the substance and the reaction product are 4-methylumbelliferyl-N-acetyl-$\alpha$-D-neuraminic acid and 4-methylumbelliferone, respectively, or a derivative containing fluorescein and fluorescein, respectively.

[17] The method according to any of [11] to [15],
wherein:
the pathogenic microorganism is at least one selected from the group consisting of coronavirus, severe acute respiratory syndrome (SARS) coronavirus, middle east respiratory syndrome (MERS) virus, mumps virus, measles virus, nipah virus, canine distemper virus, human immunodeficiency virus (HIV), hepatitis B virus, human T cell leukemia virus (HTLV), Ebola virus, hepatitis C virus, Lassa virus, hantavirus, rabies virus, Japanese encephalitis virus, yellow fever virus, dengue virus, rubella virus, rotavirus, and norovirus; and
the enzyme is at least one selected from the group consisting of hemagglutinin-esterase, neuraminidase, reverse transcriptase, and RNA-dependent RNA polymerase.

[18] The method according to any of [11] to [15], wherein the substance is at least one selected from the group consisting of a derivative containing 4-methylumbelliferone, a derivative containing fluorescein, a derivative containing resorufin, and a derivative containing rhodamine.

[19] A method for diagnosing presence or absence of infection of a pathogenic microorganism,
the method including:
a step of separating a biological sample from a subject suspected to be infected with the pathogenic microorganism;
an introducing step of introducing a hydrophilic solvent that contains the biological sample and a substance serving as a substrate for a reaction involving an enzyme present on a surface of the pathogenic microorganism or in the pathogenic microorganism into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;
an enclosing step of introducing a hydrophobic solvent into the space to form in the receptacle a droplet of the hydrophilic solvent that is covered with the hydrophobic solvent and envelopes the pathogenic microorganism and the substance; and
a detecting step of optically detecting a reaction product produced by the reaction between the enzyme and the substance in the droplet (wherein, the detection of the reaction product indicates the infection of the pathogenic microorganism),
wherein the hydrophilic solvent contains at least one of a buffering substance or trimethylamine oxide (TMAO).

[20] The method according to [19], wherein the concentrations of the buffering substance and trimethylamine oxide in the hydrophilic solvent are 1 M or more.

[21] The method according to [19] or [20], wherein the buffering substance is DEA (diethanolamine), HEPES (4-(2-hydroxyethyl)-1-piperazineethanesulfonic acid), sarcosine, or glycine.

[22] The method according to any of [19] to [21], wherein the hydrophilic solvent has a pH value greater than an acid dissociation constant (pKa) of the reaction product.

[23] The method according to any of [19] to [22], further including a step of determining the number and/or subspecies of the pathogenic microorganism based on detection intensity of the reaction product.

[24] The method according to any of [19] to [23], wherein:
the pathogenic microorganism is influenza virus;
the enzyme is neuraminidase;
the substance and the reaction product are 4-methylumbelliferyl-N-acetyl-α-D-neuraminic acid and 4-methylumbelliferone, respectively, or a derivative containing fluorescein and fluorescein, respectively, and the reaction product is 4-methylumbelliferone.

[25] The method according to any of [19] to [23], wherein:
the pathogenic microorganism is at least one selected from the group consisting of coronavirus, severe acute respiratory syndrome (SARS) coronavirus, middle east respiratory syndrome (MERS) virus, mumps virus, measles virus, nipah virus, canine distemper virus, human immunodeficiency virus (HIV), hepatitis B virus, human T cell leukemia virus (HTLV), Ebola virus, hepatitis C virus, Lassa virus, hantavirus, rabies virus, Japanese encephalitis virus, yellow fever virus, dengue virus, rubella virus, rotavirus, and norovirus; and
the enzyme is at least one selected from the group consisting of hemagglutinin-esterase, neuraminidase, reverse transcriptase, and RNA-dependent RNA polymerase.

[26] The method according to any of [19] to [23], wherein the substance is at least one selected from the group consisting of a derivative containing 4-methylumbelliferone, a derivative containing fluorescein, a derivative containing resorufin, and a derivative containing rhodamine.

[27] A method for detecting drug susceptibility of a pathogenic microorganism in a biological sample separated from a subject infected with the pathogenic microorganism or a subject suspected to be infected with the pathogenic microorganism,
the method including:
an introducing step of introducing a hydrophilic solvent that contains the biological sample, a substance serving as a substrate for a reaction involving an enzyme present on a surface of the pathogenic microorganism or in the pathogenic microorganism, and an inhibitor for the enzyme into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;
an enclosing step of introducing a hydrophobic solvent into the space to form in the receptacle a droplet of the hydrophilic solvent that is covered with the hydrophobic solvent and envelopes the pathogenic microorganism, the substance, and the inhibitor; and
a detecting step of optically detecting a reaction product produced by the reaction between the enzyme and the substance in the droplet (wherein, the case where detection intensity of the reaction product in the presence of the inhibitor is less than detection intensity of the reaction product in the absence of the inhibitor indicates that the pathogenic microorganism is sensitive to the inhibitor),
wherein the hydrophilic solvent contains at least one of a buffering substance or trimethylamine oxide (TMAO).

[28] The method according to [27], wherein the concentrations of the buffering substance and trimethylamine oxide in the hydrophilic solvent are 1 M or more.

[29] The method according to [27] or [28], wherein the buffering substance is DEA (diethanolamine), HEPES (4-(2-hydroxyethyl)-1-piperazineethanesulfonic acid), sarcosine, or glycine.

[30] The method according to any of [27] to [29], wherein the hydrophilic solvent has a pH value greater than an acid dissociation constant (pKa) of the reaction product.

[31] The method according to any of [27] to [30], wherein:
the pathogenic microorganism is influenza virus;
the enzyme is neuraminidase;
the substance and the reaction product are 4-methylumbelliferyl-N-acetyl-α-D-neuraminic acid and 4-methylumbelliferone, respectively, or a derivative containing fluorescein and fluorescein, respectively; and
the inhibitor is a neuraminidase inhibitor.

[32] A method for screening an anti-pathogenic microbial agent,
the method including:
an introducing step of introducing a hydrophilic solvent that contains a pathogenic microorganism, a substance serving as a substrate for a reaction involving an enzyme present on a surface of the pathogenic microorganism or in the pathogenic microorganism, and a candidate compound into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;
an enclosing step of introducing a hydrophobic solvent into the space to form in the receptacle a droplet of the hydrophilic solvent that is covered with the hydrophobic solvent and envelopes the pathogenic microorganism, the substance, and the candidate compound; and
a detecting step of optically detecting a reaction product produced by the reaction between the enzyme and the substance in the droplet (wherein, the case where detection intensity of the reaction product in the presence of the candidate compound is less than detection intensity of the reaction product in the absence of the candidate compound indicates that the candidate compound has anti-pathogenic microorganism activity),
wherein the hydrophilic solvent contains at least one of a buffering substance or trimethylamine oxide (TMAO).

[33] The method according to [32], wherein the concentrations of the buffering substance and trimethylamine oxide in the hydrophilic solvent are 1 M or more.

[34] The method according to [32] or [33], wherein the buffering substance is DEA (diethanolamine), HEPES (4-(2-hydroxyethyl)-1-piperazineethanesulfonic acid), sarcosine, or glycine.

[35] The method according to any of [32] to [34], wherein the hydrophilic solvent has a pH value greater than an acid dissociation constant (pKa) of the reaction product.

[36] The method according to [32] to [35],
wherein:
the pathogenic microorganism is influenza virus;
the enzyme is neuraminidase;
the substance and the reaction product are 4-methylumbelliferyl-N-acetyl-α-D-neuraminic acid and 4-methylumbelliferone, respectively, or a derivative containing fluorescein and fluorescein, respectively; and
a neuraminidase inhibitor as the candidate compound is screened.

[37] A kit for detecting a pathogenic microorganism in a biological sample separated from a subject infected with the pathogenic microorganism or a subject suspected to be infected with the pathogenic microorganism,
the kit including:
an array including a lower-layer section in which a plurality of receptacles capable of storing the pathogenic microorganism are formed separately from each other by a side wall having a hydrophobic upper surface and an upper-layer section facing a side of the lower-layer section in which side the receptacles are formed, with a space between the lower-layer section and the upper-layer section;
a substance serving as a substrate for a reaction involving an enzyme present on a surface of the pathogenic microorganism or in the pathogenic microorganism;
a hydrophilic solvent containing at least one of a buffering substance or trimethylamine oxide (TMAO); and
a hydrophobic solvent.

[38] The kit according to [37], wherein the concentrations of the buffering substance and trimethylamine oxide in the hydrophilic solvent are 1 M or more.

[39] The kit according to [37] or [38], wherein the buffering substance is DEA (diethanolamine), HEPES (4-(2-hydroxyethyl)-1-piperazineethanesulfonic acid), sarcosine, or glycine.

[40] The kit according to any of [37] to [39], wherein the hydrophilic solvent has a pH value greater than an acid dissociation constant (pKa) of the reaction product.

[41] The kit according to any of [37] to [40],
wherein:
the pathogenic microorganism is influenza virus;
the enzyme is neuraminidase;
the substance and the reaction product are 4-methylumbelliferyl-N-acetyl-α-D-neuraminic acid and 4-methylumbelliferone, respectively, or a derivative containing fluorescein and fluorescein, respectively.

[42] The kit according to any of [37] to [40],
wherein:
the pathogenic microorganism is at least one selected from the group consisting of coronavirus, severe acute respiratory syndrome (SARS) coronavirus, middle east respiratory syndrome (MERS) virus, mumps virus, measles virus, nipah virus, canine distemper virus, human immunodeficiency virus (HIV), hepatitis B virus, human T cell leukemia virus (HTLV), Ebola virus, hepatitis C virus, Lassa virus, hantavirus, rabies virus, Japanese encephalitis virus, yellow fever virus, dengue virus, rubella virus, rotavirus, and norovirus; and
the enzyme is at least one selected from the group consisting of hemagglutinin-esterase, neuraminidase, reverse transcriptase, and RNA-dependent RNA polymerase.

[43] The kit according to any of [37] to [40],
wherein:
the substance is at least one selected from the group consisting of a derivative containing 4-methylumbelliferone, a derivative containing fluorescein, a derivative containing resorufin, and a derivative containing rhodamine.

[44] A method for suppressing migration of a reaction product to a hydrophobic solvent from a hydrophilic solvent, wherein the reaction product is produced directly and released from a substrate by reacting an enzyme with a substance serving as a substrate for a reaction involving the enzyme in the hydrophilic solvent that is in interfacial contact with the hydrophobic solvent, the method including adding at least one of a buffering substance or trimethylamine oxide (TMAO) to the hydrophilic solvent.

[45] The method according to [44], wherein the concentrations of the buffering substance and trimethylamine oxide in the hydrophilic solvent are 1 M or more.

[46] The method according to [44] or [45], wherein the buffering substance is DEA (diethanolamine), HEPES (4-(2-hydroxyethyl)-1-piperazineethanesulfonic acid), sarcosine, or glycine.

[47] The method according to any of [44] to [46],
wherein the hydrophilic solvent has a pH value greater than an acid dissociation constant (pKa) of the reaction product.

In the present invention, the "pathogenic microorganism" includes bacteria and viruses. Examples of the bacteria include, but are not particularly limited to, coliform group, *vibrio parahaemolyticus, campylobacter, enterobacter*, and *bacillus* bacteria. Examples of the viruses include, but are not particularly limited to, coronavirus, SARS virus, MARS virus, influenza virus, mumps virus, measles virus, nipah virus, canine distemper virus, HIV, hepatitis B virus, HTLV, Ebola virus, hepatitis C virus, Lassa virus, hantavirus, rabies virus, yellow fever virus, dengue virus, rubella virus, rotavirus, and norovirus.

Advantageous Effect of Invention

The present invention provides a method capable of detecting a reaction product of an enzyme and a substrate with high sensitivity in a hydrophilic solvent that is in interfacial contact with a hydrophobic solvent.

DESCRIPTION OF EMBODIMENTS

Figure 1:
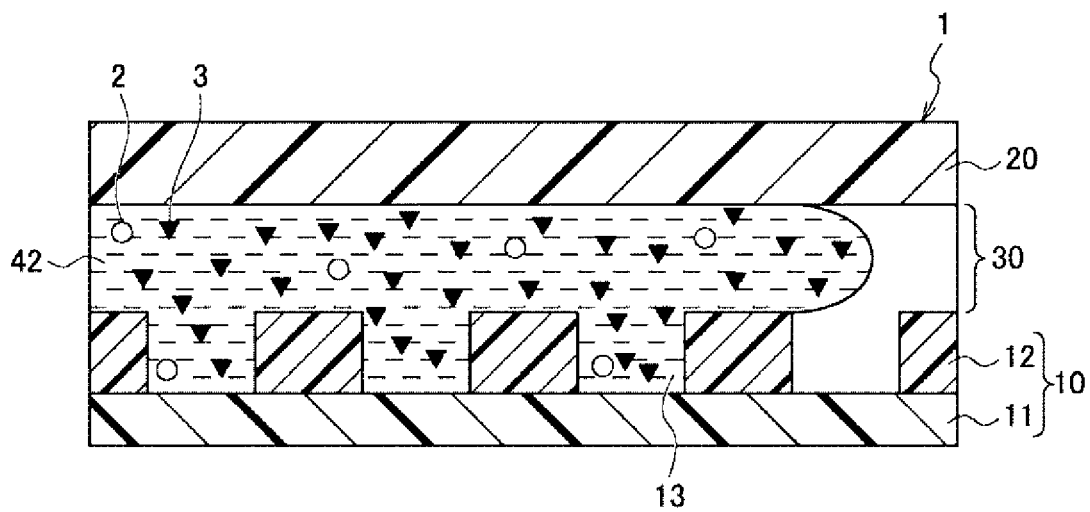
FIG. 1 is a diagram illustrating a step of one embodiment of a method for detecting an enzymatic reaction product according to the present invention (an introducing step and an enclosing step in a pathogenic microorganism detecting method).
Figure 1:
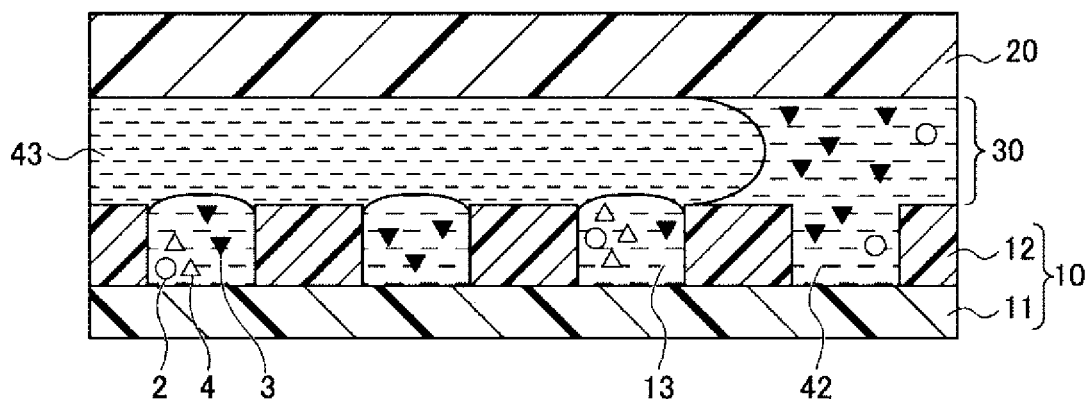
Figure 2:
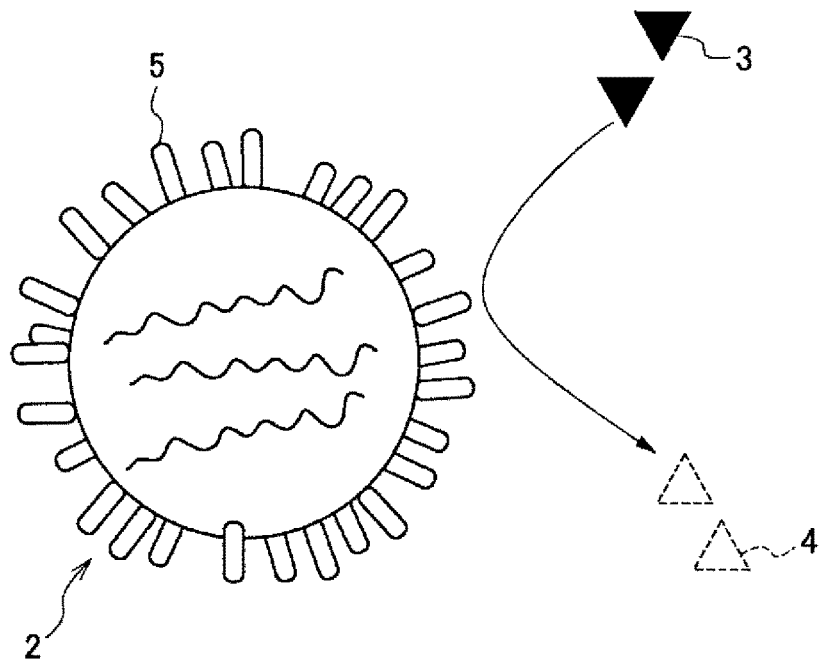
FIG. 2 is a diagram illustrating a reaction product produced as a result of a reaction between an enzyme present on the particle surface of virus and a chromogenic substrate.

Hereinafter, preferable embodiments of the present invention will be described with reference to drawings. The embodiments described below are merely typical exemplary illustrations of the present invention, and do not cause the scope of the present invention to be construed in a limited sense.

1. Method for Detecting Enzymatic Reaction Product

A method for detecting an enzymatic reaction product according to the present invention is a method for detecting a reaction product, including reacting an enzyme with a substance serving as a substrate for a reaction involving the enzyme in a hydrophilic solvent that is in interfacial contact with a hydrophobic solvent, wherein the reaction product is produced directly and released from the substrate, and wherein the hydrophilic solvent contains at least one of a buffering substance or trimethylamine oxide (trimethylamine-N-oxide: TMAO).

In the method for detecting an enzymatic reaction product according to the present invention, migration of the reaction product to the hydrophobic solvent from the hydrophilic solvent can be suppressed by adding at least one of a buffering substance or TMAO to the hydrophilic solvent.

The hydrophilic solvent is not particularly limited as long as it is conventionally used as a reaction solution of an enzyme, and for example, water or a buffer solution obtained by adding a buffering substance in a concentration required for the optimization of an enzyme reaction to water is used.

The hydrophobic solvent capable of being suitably used is, for example, at least one selected from the group consisting of saturated hydrocarbon, unsaturated hydrocarbon, aromatic hydrocarbon, silicone oil, perfluorocarbon, halogen solvents, and hydrophobic ionic liquid, or a mixture including the at least one. Examples of the saturated hydrocarbon include alkane and cycloalkane. Examples of the alkane include decane and hexadecane. Examples of the unsaturated hydrocarbon include squalene. Examples of the aromatic hydrocarbon include benzene and toluene. Examples of the perfluorocarbon include Fluorinert® FC40 (manufactured by SIGMA). Examples of the halogen solvents include chloroform, methylene chloride, and chlorobenzene. The hydrophobic ionic liquid denotes ionic liquid that is not dissociated at least in water. Examples of the ionic liquid include 1-butyl-3-methylimidazolium hexafluorophosphate. The ionic liquid denotes a salt that is in the form of liquid at room temperature.

The reaction between an enzyme and a substrate in a hydrophilic solvent that is in interfacial contact with a hydrophobic solvent is not particularly limited, and typical examples thereof include an ELISA method and a PCR method that are performed in a water-in-oil type emulsion. In particular, a digital ELISA method and a digital PCR method that provide a reaction in an emulsion having a minimal volume are known.

The substrate only needs to produce a reaction product having, after the reaction, different optical characteristics from those before the reaction of the substrate with the enzyme. The substrate to be used may be a substance having, after the reaction, absorbance or optical rotation changed from that before the reaction, and a substance exhibiting fluorescence after the reaction.

In particular, the substrate to be used may be a substrate directly releasing a reaction product upon a reaction between the substrate and an enzyme having substrate cleavage activity. Examples of the substrate include a substrate that causes the cleavage of the substrate due to the enzyme to release a reaction product as a chromophoric group.

The "enzyme having substrate cleaving activity" is not particularly limited as long as it can cleave a substrate and realize the release of a reaction product (specifically described later). As the "enzyme having substrate cleaving activity", for example, enzymes belonging to transferases classified in EC2 (EC number stands for Enzyme Commission Number) and hydrolases classified in EC3 and lyases classified in EC4 can be used. Specific examples of combinations of enzymes and substrates thereof (and sites to be cleaved in the substrates) will be given below.

TABLE 1

| Enzyme | Substrate (site to be cleaved in substrate) |
|---|---|
| Esterase | Ester bond or bond derived from ester bond |
| Glucosidase | Glycoside bond or bond derived from glycoside bond |
| Phosphatase | Phosphoester bond or bond derived from phosphoester bond |
| DNAase | DNA or derivative thereof |
| RNAase | RNA or derivative thereof |
| Protease | Peptide bond or bond derived from peptide bond |

The substrate to be used may be a derivative containing 4-methylumbelliferone, a derivative containing fluorescein, a derivative containing resorufin, a derivative containing rhodamine, and the like which have a site to be cleaved by an enzyme and release a fluorescent substance as a reaction product upon the cleavage.

In the reaction between the enzyme and the substrate in the hydrophilic solvent that is in interfacial contact with the hydrophobic solvent, at least one of a buffering substance or TMAO is added to the hydrophilic solvent in order to detect the reaction product produced in the hydrophilic solvent with high sensitivity. This can suppress the distribution (leakage) of the reaction product to the hydrophobic solvent from the hydrophilic solvent, to accumulate the reaction product in a high concentration in the hydrophilic solvent, whereby the reaction product can be detected with high sensitivity.

The buffering substance is not particularly limited, and a so-called good's buffer such as MES (2-morpholinoethanesulfonic acid), ADA (N-(2-acetamido)iminodiacetic acid), PIPES (piperazine-1,4-bis(2-ethanesulfonic acid)), ACES (N-(2-acetamido)-2-aminoethanesulfonic acid), BES (N,N-bis(2-hydroxyethyl)-2-aminoethanesulfonic acid), TES (N-tris(hydroxymethyl)methyl-2-aminoethanesulfonic acid), or HEPES (4-(2-hydroxyethyl)-1-piperazineethanesulfonic acid), and Tris(tris(hydroxymethyl)aminomethane), DEA (diethanolamine), glycine, sarcosine (N-methylglycine), phosphoric acid, or the like may be used. These buffering substances may be used singly or in combinations of two or more.

As the buffering substance, DEA, HEPES, glycine, and sarcosine are preferred, and DEA and HEPES are more preferred. In particular, DEA is used in combination with fluorescein as the reaction product, which exhibits a prominent effect (see Test Example 4).

The leakage of the reaction product to the hydrophobic solvent from the hydrophilic solvent can be more effectively prevented by setting the concentrations of the buffering substance and/or TMAO in the hydrophilic solvent to be equal to or greater than a predetermined concentration. Specifically, in view of suppressing the leakage of the reaction product to the hydrophobic solvent from the hydrophilic solvent, the concentrations of the buffering substance and TMAO are, for example, 100 mM or more, more preferably 500 mM or more, and still more preferably 1 M or more. The upper limit of the concentration is not particularly limited, and only needs to be a necessary and sufficient value for providing the effects of the present invention.

A compound that can exhibit the same function as that of TMAO can also be used in order to suppress the leakage of the reaction product to the hydrophobic solvent from the hydrophilic solvent.

2. Pathogenic Microorganism Detecting Method

A method for detecting enzymatic reaction product according to the present invention may be used to detect a pathogenic microorganism in a biological sample separated from a subject infected with the pathogenic microorganism or a subject suspected to be infected with the pathogenic microorganism. The pathogenic microorganism detecting method according to the present invention includes the following steps:

(1A) an introducing step of introducing a hydrophilic solvent that contains the biological sample and a substance serving as a substrate for a reaction involving an enzyme present on a particle surface of the pathogenic microorganism or in the pathogenic microorganism into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;

(2A) an enclosing step of introducing a hydrophobic solvent into the space to form in the receptacle a droplet of the hydrophilic solvent that is covered with the hydrophobic solvent and envelopes the pathogenic microorganism and the substance; and (3A) a detecting step of optically detecting a reaction product produced by the reaction between the enzyme and the substance in the droplet.

In the present invention, the biological sample is not particularly limited as long as the biological sample is a biologically derived material that may contain the pathogenic microorganism to be detected. Examples of the biological sample include nasal aspirates, nasal swabs, pharyngeal swabs, throat swabs, saliva, sputum, blood (including whole blood, serum, and plasma), urine, cells, tissues, and extract liquids of organs.

The pathogenic microorganism is not particularly limited as long as the pathogenic microorganism has an enzyme on a surface of the pathogenic microorganism or in the pathogenic microorganism, and produces a reaction product that can be optically detected as a result of a reaction involving the enzyme. More specifically, the pathogenic microorganism may have an enzyme having substrate cleavage activity to a chromogenic substrate on a surface of the pathogenic microorganism or in the pathogenic microorganism, and causes the cleavage of the chromogenic substrate due to the enzyme to release a reaction product as a chromophoric group. The pathogenic microorganism may have an enzyme having activity for bonding monomers as substrates each other to produce a polymer on a surface of the pathogenic microorganism or in the pathogenic microorganism, the polymer produced due to the enzyme being a reaction product as a chromophoric group. Examples of combinations of the pathogenic microorganisms and enzymes thereof will be given below.

TABLE 2

| | |
|---|---|
| Coronavirus | Hemagglutinin-esterase |
| SARS | Hemagglutinin-esterase |
| MARS | Hemagglutinin-esterase |
| Mumps virus (Mumps) | Neuraminidase |
| Measles virus | Neuraminidase |
| Nipah virus | Neuraminidase |
| Canine distemper virus | Neuraminidase |
| HIV | Reverse transcriptase |
| Hepatitis B | Reverse transcriptase |
| HTLV | Reverse transcriptase |
| Ebola virus | RNA-dependent RNA polymerase |
| Hepatitis C | RNA-dependent RNA polymerase |
| Lassa virus | RNA-dependent RNA polymerase |
| Hantavirus | RNA-dependent RNA polymerase |
| Rabies virus | RNA-dependent RNA polymerase |
| Japanese encephalitis virus | RNA-dependent RNA polymerase |
| Yellow fever virus | RNA-dependent RNA polymerase |
| Dengue virus | RNA-dependent RNA polymerase |
| Rubella virus | RNA-dependent RNA polymerase |
| Rotavirus | RNA-dependent RNA polymerase |
| Norovirus | RNA-dependent RNA polymerase |
| Coliform group | Galactosidase, Glucuronidase |
| *Vibrio parahaemolyticus* | Trypsin |
| *Campylobacter* | Galactosidase |
| *Enterobacter* | Galactosidase |
| *Bacillus circulance* | Xylosidase |
| *Bacillus subtilis* | Chymotrypsin |

[Introducing Step (A1)]

The introducing step (A1) will be described with reference to FIG. 1A. In the present embodiment, the case where the pathogenic microorganism detecting method according to the present invention is carried out by use of an array will be described. The array includes a lower-layer section in which a plurality of receptacles capable of storing the pathogenic microorganism (hereinafter, virus will be described as an example) are formed separately from each other by a side wall having a hydrophobic upper surface and an upper-layer section facing a side of the lower-layer section in which side the receptacles are formed, with a space between the lower-layer section and the upper-layer section.

In a lower-layer section 10 of an array 1, a plurality of receptacles 13 capable of storing virus particles are formed separately from each other by a side wall 12 having a hydrophobic upper surface. An upper-layer section 20 faces a side of the lower-layer section 10 in which side the receptacles 13 are formed.

In this step, a hydrophilic solvent 42 is introduced into a space 30 between the lower-layer section 10 and the upper-layer section 20. The hydrophilic solvent 42 may contain virus 2 derived from a biological sample. The hydrophilic solvent 42 contains a substance 3 (hereinafter, referred to as a "substrate 3") serving as a substrate for a reaction involving an enzyme present on the particle surface of the virus 2 (or in the virus 2). The hydrophilic solvent 42 can be introduced into the space 30 from a through-hole (not shown) formed in at least one of the upper-layer section 20 and the lower-layer section 10, for example. The hydrophilic solvent 42 introduced into the space 30 flows in a direction in parallel with surfaces of the lower-layer section 10 and the upper-layer section 20, the surfaces of the lower-layer section 10 and the upper-layer section 20 facing each other, as shown in the figure.

Water is used as the hydrophilic solvent 42. The hydrophilic solvent 42 preferably has a pH value greater than an acid dissociation constant (pKa) of the reaction product produced from the substrate 3 (this will be described later in detail).

The substrate 3 only needs to produce a reaction product having different optical characteristics from those before the reaction of the substrate 3 with the enzyme after the reaction. The substrate 3 to be used may be a substance having absorbance and optical rotation changed before and after the reaction, and a substance exhibiting fluorescence after the reaction. The substrate 3 will be described later in detail.

The hydrophilic solvent 42 contains at least one of a buffering substance or TMAO. By setting the concentration of the buffering substance or TMAO in the hydrophilic solvent 42 to be equal to or greater than a predetermined concentration, the reaction product can be detected with higher sensitivity in a detecting step (3) (this will be described later in detail). The hydrophilic solvent 42 may contain another buffering substance in a concentration required for optimizing the reaction between the enzyme and the substrate 3 (usually a significantly lower concentration than the predetermined concentration) in addition to the buffering substance contained in the predetermined concentration.

The buffering substance is not particularly limited, and a so-called good's buffer such as MES (2-morpholinoethane-sulfonic acid), ADA (N-(2-acetamido)iminodiacetic acid), PIPES (piperazine-1,4-bis(2-ethanesulfonic acid)), ACES (N-(2-acetamido)-2-aminoethanesulfonic acid), BES (N,N-bis(2-hydroxyethyl)-2-aminoethanesulfonic acid), TES (N-tris(hydroxymethyl)methyl-2-aminoethanesulfonic acid), or HEPES (4-(2-hydroxyethyl)-1-piperazineethane-sulfonic acid), and Tris(tris(hydroxymethyl)aminomethane), DEA (diethanolamine) or the like may be used.

The hydrophilic solvent 42 may contain a surfactant. When the hydrophilic solvent 42 contains the surfactant, the enzyme present in the virus 2 may be exposed from the surface. When the hydrophilic solvent 42 contains the surfactant, the hydrophilic solvent 42 tends to be easily introduced into the space 30 and the receptacles 13.

Examples of the surfactant include, but are not particularly limited to, TWEEN 20 (CAS No. 9005-64-5, polyoxyethylene sorbitan monolaurate) and Triton X-100 (CAS No. 9002-93-1, general name: polyethylene glycol mono-4-octylphenyl ether (n≈10)). The concentration of the surfactant added to the first solvent 20 is not particularly limited, and the concentration is preferably 0.01 to 1%.

Furthermore, an anionic surfactant, a cationic surfactant, a nonionic surfactant, a zwitterionic surfactant, a surfactant derived from nature or the like can be widely used as the surfactant.

The anionic surfactant is classified, for example, into a carboxylic type, a sulfate type, a sulfonic type, and a phosphate type. Specific examples thereof include sodium dodecyl sulfate, sodium laurate, sodium α-sulfo fatty acid methyl ester, sodium dodecylbenzenesulfonate, and sodium dodecylethoxylate sulfate, and among these, sodium dodecylbenzenesulfonate is preferably used.

The cationic surfactant is classified, for example, into a quaternary ammonium salt type, an alkylamine type, and a heterocyclic amine type. Specific examples thereof include stearyltrimethylammonium chloride, distearyldimethylammonium chloride, didecyldimethylammonium chloride, cetyltripyridinium chloride, and dodecyldimethylbenzylammonium chloride.

Examples of the nonionic surfactant include polyoxyethylene alkyl ether, polyoxyethylene hydrogenated castor oil, polyoxyethylene mono fatty acid ester, polyoxyethylene sorbitan mono fatty acid ester, sucrose fatty acid ester, polyglyceryl fatty acid ester, alkyl polyglucoside, and N-methylalkyl glucamide. Among these, preferred are nonionic surfactants commercially available under the names of Triton X (Triton X-100 or the like), Pluronic® (Pluronic F-123, F-68 or the like), Tween (Tween 20, 40, 60, 65, 80, 85 or the like), Brij® (Brij 35, 58, 98 or the like), and Span (Span 20, 40, 60, 80, 83, and 85) in addition to dodecyl alcohol ethoxylate, nonylphenol ethoxylate, and lauroyl diethanol amide.

Examples of the amphoteric surfactant include lauryldimethyl aminoacetic acid betaine, dodecylaminomethyldimethylsulfopropyl betaine, and 3-(tetradecyldimethylaminio) propane-1-sulfonate, and preferred examples thereof to be used include 3-[(3-cholamidopropyl)dimethylammonio]-1-propane sulfonate (CHAPS) and 3-[(3-cholamidopropyl)dimethylammonio]-2-hydroxy-1-propane sulfonate (CHAPSO).

The surfactant derived from nature is preferably, for example, lecithin or saponin. Among compounds called lecithin, preferred are specifically phosphatidylcholine, phosphatidylethanolamine, phosphatidylinositol, phosphatidylserine, phosphatidic acid, and phosphatidylglycerol. Quillaja saponin is preferable as saponin.

The virus 2 and the substrate 3 enter the receptacles 13 according to this step. When the virus 2 is diluted into a sufficiently low concentration in the hydrophilic solvent 42, the number of the viruses 2 entering one receptacle 13 may be 0 or at most 1. When the concentration of the viruses 2 is higher in the hydrophilic solvent 42, two or more viruses 2 may be introduced into one receptacle 13.

[Enclosing Step (A2)]

The enclosing step (2) will be described with reference to FIG. 1B. In this step, a hydrophobic solvent 43 is introduced into the space 30 between the lower-layer section 10 and the upper-layer section 20.

The hydrophobic solvent 43 is any solvent (immiscible solvent) that is difficult to be mixed with the hydrophilic solvent 42 used in the introducing step (1). The hydrophobic solvent 43 capable of being suitably used is, for example, at least one selected from the group consisting of saturated hydrocarbon, unsaturated hydrocarbon, aromatic hydrocarbon, silicone oil, perfluorocarbon, halogen solvents, and hydrophobic ionic liquid, or a mixture including the at least one. Examples of the saturated hydrocarbon include alkane and cycloalkane. Examples of the alkane include decane and hexadecane. Examples of the unsaturated hydrocarbon include squalene. Examples of the aromatic hydrocarbon include benzene and toluene. Examples of the perfluorocarbon include Fluorinert® FC40 (manufactured by SIGMA). Examples of the halogen solvents include chloroform, methylene chloride, and chlorobenzene. The hydrophobic ionic liquid denotes ionic liquid that is not dissociated at least in water. Examples of the ionic liquid include 1-butyl-3-methylimidazolium hexafluorophosphate. The ionic liquid denotes a salt that is in the form of liquid at room temperature.

The hydrophobic solvent 43 may be introduced into the space 30 via a through-hole (not shown) formed in at least one of the upper-layer section 20 and the lower-layer section 10 as with the hydrophilic solvent 42. The hydrophobic solvent 43 introduced into the space 30 flows in a direction in parallel with surfaces of the lower-layer section 10 and the upper-layer section 20, the surfaces of the lower-layer section 10 and the upper-layer section 20 facing each other, as shown in the figure, and the hydrophilic solvent 42 in the space 30 is thus replaced by the hydrophobic solvent 43.

This causes a droplet of the hydrophilic solvent 42 covered with the hydrophobic solvent 43 and enveloping the virus 2 and the substrate 3 to be formed in the receptacles 13.

The enzyme and the substrate 3 co-exist in the minimum volume of the droplet of the hydrophilic solvent 42, and a reaction between the enzyme present on the particle surface of the virus 2 or in the virus 2 and the substrate 3 proceeds to produce a reaction product 4. With reference to FIG. 2, this will be described in detail. An enzyme 5 is present on the particle surface of the virus 2 or in the virus 2 (the case where the enzyme 5 is present on the surface of the virus is shown in the figure). When the substrate 3 is contacted and reacted with the enzyme 5, the reaction product 4 is produced. The reaction product 4 exhibits different optical characteristics from those of the substrate 3, and exhibits, for example, the shift of absorbance or optical rotation, and luminescence (fluorescence).

The virus 2 and the substrate 3 are enclosed into the droplet having the minimum volume according to this step, whereby the reaction between the enzyme 5 and the substrate 3 causes the reaction product 4 to be produced in the minimum volume in the droplet. This allows the optical detection of the reaction product 4. The volume of the receptacle 13 (that is, the volume of the droplet of the hydrophilic solvent 42) is not particular limited, and is, for example, 10 aL to 100 nL, and preferably 1 fL to 1 pL.

The case where the virus 2 is influenza virus (see Table 1), and 4-methylumbelliferyl-N-acetyl-α-D-neuraminic acid (4 MU-NANA) is used for the substrate 3 will be specifically described as an example.

Neuraminidase (enzyme 5) is present on the particle surface of influenza virus. When 4 MU-NANA (substrate 3) is contacted and reacted with neuraminidase, 4-methylumbelliferone (reaction product 4) as a fluorescent substance is produced.

4-methylumbelliferone (4 MU) derived from the hydrolysis of 4 MU-NANA due to neuraminidase is produced as a chromophoric group represented by the following formula and exhibiting fluorescence. The substrate 3 is not limited to 4 MU-NANA as long as the substrate 3 releases the chromophoric group that can be optically detected by the hydrolysis of neuraminic acid due to neuraminidase, and conventionally known substrates can be used. 4 MU of the reaction product 4 has a hydroxyl group, as represented by the following formula.

[Chemical Formula 1]

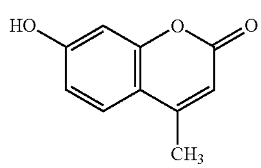

In the detecting method according to the present invention, the pH value of the hydrophilic solvent 42 is preferably set higher than the acid dissociation constant (pKa) of 4 MU, i.e. 7.79, in order to desorb hydrogen from the hydroxyl group of 4 MU so that 4 MU has a charge. By desorbing the hydrogen from the hydroxyl group of 4 MU, 4 MU contained in the droplet of the hydrophilic solvent 42 covered with the hydrophobic solvent 43 cannot distribute to the hydrophobic solvent 43 because of the charge, and as a result of this, 4 MU is accumulated in a high concentration in the droplet of the hydrophilic solvent 42.

If the pH value of the hydrophilic solvent 42 is less than the acid dissociation constant (pKa) of 4 MU, 4 MU has a hydroxyl group, whereby 4 MU has no charge or a smaller charge than that in the case where the hydrogen is desorbed from the hydroxyl group. When 4 MU contained in the droplet of the hydrophilic solvent 42 has no charge, or when 4 MU has a small charge, 4 MU is apt to distribute to the hydrophobic solvent 43 that is in interfacial contact with the hydrophilic solvent 42, which causes 4 MU to be lost from the droplet of the hydrophilic solvent 42, or a 4 MU concentration in the droplet to be decreased.

Heretofore, the reaction between neuraminidase and 4 MU-NANA has been performed under a pH condition of about 5, which is the optimal pH of an enzyme reaction involving neuraminidase, and released 4 MU has been detected under a pH condition of about 10, which is a pH at which the fluorescence efficiency (quantum efficiency) of 4 MU is maximized. Meanwhile, in the present invention, both the reaction between neuraminidase and 4 MU-NANA and the detection of 4 MU are performed under a pH condition higher than pKa 7.79 of 4 MU, which is one of technical features of the present invention.

If the substrate 3 and the enzyme 5 are contacted with each other even before this step, the reaction between the substrate 3 and the enzyme 5 may proceed, but before the droplet of the hydrophilic solvent 42 enveloping the virus 2 and the substrate 3 is formed in this step, the produced reaction product 4 is not accumulated in the minimum volume. For this reason, in the optical detection of the reaction product 4, the influence of the reaction product 4 produced before the enclosing step (2) is negligibly small.

Examples of the chromogenic substrate that may disadvantageously cause the distribution of the reaction product 4 to the hydrophobic solvent 43 coating the droplet of the hydrophilic solvent 42 from the droplet in a similar fashion, in addition to 4-methylumbelliferyl-N-acetyl-α-D-neuraminic acid containing 4 MU, include the following chromogenic substrates.

The chromogenic substrate is a derivative containing 4-methylumbelliferone, and excludes 4 MU-NANA. Herein, the "derivative" means a compound having 4 MU as a "chromophoric group" and a "substrate" to be cleaved by the reaction with the enzyme 5 in a structure.

The chromogenic substrate is a derivative containing fluorescein as a chromophoric group. If the derivative is contacted and reacted with the enzyme 5, the substrate is cleaved by the enzyme 5, and fluorescein (pKa: 6.4) as a fluorescent substance is released as the reaction product 4. The structure of fluorescein is shown below.

[Chemical Formula 2]

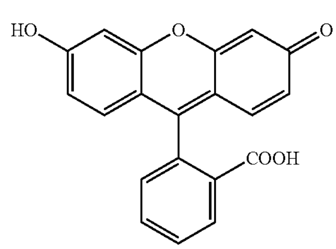

The chromogenic substrate is a derivative containing resorufin as a chromophoric group. If the derivative is contacted and reacted with the enzyme 5, the substrate is cleaved by the enzyme 5, and resorufin (pKa: 6.0) as a fluorescent substance is released as the reaction product 4. The structure of resorufin is shown below.

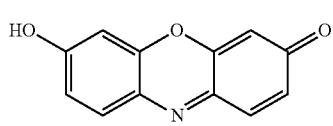

[Chemical Formula 3]

The chromogenic substrate is a derivative containing rhodamine as a chromophoric group. If the derivative is contacted and reacted with the enzyme 5, the substrate is cleaved by the enzyme 5, and rhodamine (pKa: 6.0) as a fluorescent substance is released as the reaction product 4. The structure of rhodamine is shown below.

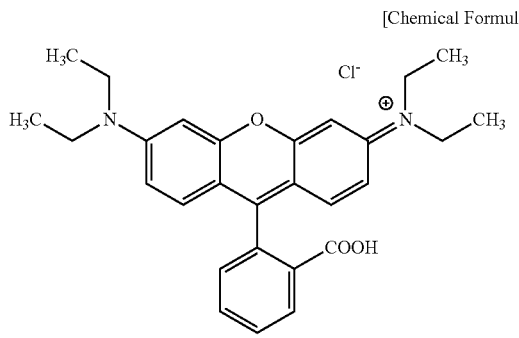

[Chemical Formula 4]

When each of these derivatives is used as the substrate 3, the pH value of the hydrophilic solvent 42 is set higher than the acid dissociation constant (pKa) of the reaction product 4 produced from the derivative. This provides the reaction product 4 having a charge, and prevents the distribution (leakage) of the reaction product 4 to the hydrophobic solvent 43, whereby the reaction product 4 can be accumulated in a high concentration in the droplet of the hydrophilic solvent 42 (see Test Example 1).

The leakage of the reaction product 4 to the hydrophobic solvent 43 from the droplet of the hydrophilic solvent 42 can also be effectively prevented by setting the concentrations of the buffering substance and/or TMAO in the hydrophilic solvent 42 to be equal to or higher than a predetermined concentration (see Test Examples 2 to 5). In view of suppressing the leakage of the reaction product 4 to the hydrophobic solvent 43 from the droplet of the hydrophilic solvent 42, the concentrations of the buffering substance and TMAO are, for example, 100 mM or more, more preferably 500 mM or more, and still more preferably 1 M or more.

In view of suppressing the leakage of the reaction product 4 to the hydrophobic solvent 43 from the droplet of the hydrophilic solvent 42, as the buffering substance, DEA, HEPES, glycine, and sarcosine are preferred, and DEA and HEPES are more preferred. In particular, DEA is used in combination with fluorescein as the reaction product 4, which exhibits a prominent effect (see Test Example 4).

A compound that can exhibit the same function as that of TMAO can also be used in order to suppress the leakage of the reaction product 4 to the hydrophobic solvent 43 from the droplet of the hydrophilic solvent 42.
[Detecting Step (A3)]

In this step, the reaction product 4 produced in the droplet of the hydrophilic solvent 42 is optically detected.

The reaction product 4 can be optically detected by use of known means capable of detecting a difference in optical characteristics between the substrate 3 and the reaction product 4. For example, the reaction product 4 can be optically detected by detecting the shift of specific absorbance or optical rotation by use of an image sensor, an absorption spectrometer, or a polarimeter, and detecting a specific fluorescence wavelength by use of an image sensor, a fluorescence microscope, or a fluorometer.

When the virus 2 is influenza virus, and 4 MU-NANA is used for the substrate 3, produced 4 MU (reaction product 4) is subjected to fluorescence detection.

Based on the detection intensity (for example, fluorescence intensity) of the detected reaction product 4 (for example, 4 MU), the number of particles and/or subspecies (subtypes) of the virus can be determined.

Specifically, in the case of influenza virus, an enzymatic activity value of neuraminidase is first calculated by use of the detected fluorescence intensity, and a standard curve specifying the relationship between fluorescence intensity created previously and neuraminidase activity. Next, the number of particles of influenza virus is quantified by use of the calculated enzymatic activity value, and a standard curve specifying the relationship between an enzymatic activity value created previously and the number of particles of the virus. This allows the amount of virus to be also quantitatively determined (analog quantitative determination), in addition to the determination as to whether the virus is contained in the biological sample separated from the subject, whereby the presence or absence and intensity of infection of influenza virus in the subject can be diagnosed. The standard curve to be used may directly specify the relationship between the fluorescence intensity and the number of particles of the virus.

For example, in influenza virus, A type virus has been known to have higher neuraminidase activity than that of B type virus. The present inventors have used the detecting method according to the present invention, and have found that the neuraminidase activity of the A type virus differs by a factor of about 2 from that of the B type virus, and both the A type virus and the B type virus can be effectively distinguished and detected based on the magnitude of the activity value. In such a case, first, an enzymatic activity value of neuraminidase is calculated by use of the detected fluorescence intensity, and a standard curve specifying the relationship between fluorescence intensity created previously and neuraminidase activity. Next, the subtype of influenza virus can be determined by use of the calculated enzymatic activity value, and the relational formula between an enzymatic activity value created previously and the subtype. For example, when the calculated enzymatic activity value is equal to or greater than a standard value, influenza virus can be determined as A type, and when the calculated enzymatic activity value is less than the standard value, influenza virus can be determined as B type. This allows the subtype of virus to be also determined, in addition to the determination as to whether the virus is contained in the biological sample separated from the subject, whereby the subtype of infection influenza virus in the subject can be diagnosed. The relational formula to be used may directly specify the relationship between the fluorescence intensity and the subtype.

Furthermore, as described above, when the virus 2 is diluted into a sufficiently low concentration in the hydrophilic solvent 42, the number of the viruses 2 entering one receptacle 13 may be 0 or at most 1. In this case, by use of a ratio between the number of the receptacles 13 in which the reaction product 4 is detected and the number of the receptacles 13 in which the reaction product 4 is not detected, the amount of virus can also be quantitatively determined based on the standard curve specifying the relationship between the ratio created previously and the number of particles of the virus (digital quantitative determination).

In the enclosing step (2), the reaction product 4 can be accumulated in a high concentration in the droplet of the hydrophilic solvent 42, whereby the reaction product 4 can be detected with high sensitivity even when only one particle of the virus 2 is contained in the receptacle 13. Therefore, according to the detecting method according to the present invention, even virus very slightly contained in the biological sample can be detected with high sensitivity, whereby the amount of the pathogenic microorganism can be determined with high accuracy.

When the reaction product 4 is accumulated in a high concentration in the droplet of the hydrophilic solvent 42, high fluorescence intensity is obtained, whereby a simple imaging device having comparatively low sensitivity can be used in optical detection. Therefore, it is expected to allow optical detection due to, for example, a camera or the like mounted on a smart phone. The optical detection due to the simple imaging device such as the camera mounted on the smart phone can make it easy to carry out a method for detecting a pathogenic microorganism according to the present invention in a comparatively small hospital, a clinic, and an individual. Furthermore, detection information on the pathogenic microorganism may be transmitted to a server, by use of communication means included in the smart phone, to analyze accumulated information (big data), and it is thus expected to allow the grasp and prediction of an endemic region, a period, a subtype or the like.

In the above, the case where the virus 2 and the substrate 3 are influenza virus and 4 MU-NANA, respectively, has been described as an example. In the present invention, for example, when coronavirus, severe acute respiratory syndrome (SARS) coronavirus, or middle east respiratory syndrome (MERS) virus is detected, the substrate 3 is any substrate that is hydrolyzed by hemagglutinin-esterase (enzyme 5) on the surface of the virus to release the above chromophoric group (reaction product 4).

For example, when human immunodeficiency virus (HIV), hepatitis B virus, or human T cell leukemia virus (HTLV) is detected, the substrate 3 may be a nucleic acid monomer polymerized by a reverse transcriptase (enzyme 5) on the surface of the virus or in the virus. A fluorescent dye may be labeled to the nucleic acid monomer, whereby fluorescence intensity increased as compared with the nucleic acid monomer is detected in a nucleic acid chain as a reaction product provided by polymerization. Similarly, for example, when Ebola virus, hepatitis C virus, Lassa virus, hantavirus, rabies virus, Japanese encephalitis virus, yellow fever virus, dengue virus, rubella virus, rotavirus, or norovirus is detected, the substrate 3 to be used can be obtained by labeling a fluorescent dye to a nucleic acid monomer to be polymerized by RNA-dependent RNA polymerase (enzyme 5) on the surface of the virus or in the virus. Not only a constitution providing fluorescence intensity increased with the polymerization of the nucleic acid monomer to the nucleic acid chain but also a constitution providing by the reaction optical characteristics (absorbance, optical rotation, fluorescence or the like) different from those before the reaction can be widely adopted.

Thus, in the detecting method according to the present invention, the substrate can be appropriately selected by the enzyme present on the surface of the pathogenic microorganism to be detected or in the pathogenic microorganism. According to pKa of the selected reaction product, the hydrophilic solvent used in the introducing step (1) is preferably selected such that the pH value of the hydrophilic solvent is higher than the pKa of the reaction product.

The substrate may be differently designed depending on the substrate specificity of the enzyme of pathogenic microorganisms even if they have the same enzyme (neuraminidase) as in, for example, influenza virus and mumps virus. For example, 4 MU-NANA is used as a chromogenic substrate for detecting influenza virus; on the other hand, a chromophoric group produced by the hydrolysis of 4 MU-NANA as a chromogenic substrate for detecting mumps virus is changed into other fluorescent substance such as fluorescein from 4 MU and such a modified substrate is used. Thus, by modifying the substrate in such manner, the affinity of each of the chromogenic substrates for neuraminidase may be differentiated between the enzyme of influenza virus and the enzyme of mumps virus, which are the same kind of enzyme. This can make it possible to distinguishably detect both the viruses in the detecting method according to the present invention.

3. Method for Detecting Drug Susceptibility of Pathogenic Microorganism

A method for detecting drug susceptibility of a pathogenic microorganism in a biological sample separated from a subject infected with the pathogenic microorganism or a subject suspected to be infected with the pathogenic microorganism according to the present invention includes the following steps:

(B1) an introducing step of introducing a hydrophilic solvent that contains the biological sample, a substance serving as a substrate for a reaction involving an enzyme present on a surface of the pathogenic microorganism or in the pathogenic microorganism, and an inhibitor for the enzyme into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;

(B2) an enclosing step of introducing a hydrophobic solvent into the space to form in the receptacle a droplet of the hydrophilic solvent that is covered with the hydrophobic solvent and envelopes the pathogenic microorganism, the substance, and the inhibitor; and (B3) a detecting step of optically detecting a reaction product produced by the reaction between the enzyme and the substance in the droplet (wherein, the case where detection intensity of the reaction product in the presence of the inhibitor is less than detection intensity of the reaction product in the absence of the inhibitor indicates that the pathogenic microorganism is sensitive to the inhibitor).

[Introducing Step (B1)]

The introducing step (B1) of the method for detecting the drug susceptibility of the pathogenic microorganism according to the present invention is different from the introducing step (A1) of the pathogenic microorganism detecting method only in that the enzyme inhibitor to be evaluated for the drug susceptibility is contained in the hydrophilic solvent. In the introducing step (B1), in addition to the pathogenic microorganism and the substrate, the inhibitor for the enzyme present on the surface of the pathogenic microorganism or in the pathogenic microorganism enters the receptacles.

[Enclosing Step (B2)]

The operation of the enclosing step (B2) of the method for detecting the drug susceptibility of the pathogenic microorganism according to the present invention is the same as the enclosing step (A2) of the pathogenic microorganism detecting method. In the enclosing step (B2), the droplet of the hydrophilic solvent covered with the hydrophobic solvent and enveloping the pathogenic microorganism, the substrate, and the inhibitor is formed in the receptacles.

[Detecting Step (B3)]

In the detecting step (B3) of the method for detecting the drug susceptibility of the pathogenic microorganism according to the present invention, the reaction product produced in the droplet of the hydrophilic solvent is optically detected in the same manner as in the detecting step (A3) of the pathogenic microorganism detecting method.

The case where the detection intensity of the reaction product in the presence of the inhibitor is reduced as compared to the detection intensity of the reaction product in the absence of the inhibitor indicates that the production of the reaction product in the droplet of the hydrophilic solvent is suppressed by the inhibitor. That is, the enzyme contained in the pathogenic microorganism is inhibited, which indicates that the pathogenic microorganism is sensitive to the inhibitor.

Meanwhile, the case where the detection intensity of the reaction product in the presence of the inhibitor is comparable with the detection intensity of the reaction product in the absence of the inhibitor indicates that the production of the reaction product in the droplet of the hydrophilic solvent is not suppressed by the inhibitor. That is, the enzyme contained in the pathogenic microorganism is not inhibited, which indicates that the pathogenic microorganism has resistance to the inhibitor.

Specifically, by use of, for example, 4 MU-NANA as the substrate and a neuraminidase inhibitor (oseltamivir, zanamivir or the like) as the inhibitor when the pathogenic microorganism is influenza virus, 4 MU to be produced for two test groups in which conditions excluding the presence and absence conditions of the neuraminidase inhibitor are made to be the same is subjected to fluorescence detection. The case where the detection intensity of 4 MU in the presence of the neuraminidase inhibitor is reduced as compared to the detection intensity of 4 MU in the absence of the neuraminidase inhibitor indicates that the production of 4 MU in the droplet of the hydrophilic solvent is suppressed by the neuraminidase inhibitor. That is, neuraminidase contained in influenza virus is inhibited, which indicates that influenza virus is sensitive to the neuraminidase inhibitor.

Meanwhile, the case where the detection intensity of 4 MU in the presence of the neuraminidase inhibitor is comparable with the detection intensity of 4 MU in the absence of the neuraminidase inhibitor indicates that the production of 4 MU in the droplet of the hydrophilic solvent is not suppressed by the neuraminidase inhibitor. That is, neuraminidase contained in influenza virus is not inhibited, which indicates that influenza virus has resistance to the neuraminidase inhibitor.

In the combinations of the pathogenic microorganisms and enzyme inhibitors that can detect the drug susceptibility, when the pathogenic microorganism of interest is coronavirus, severe acute respiratory syndrome (SARS) coronavirus, or middle east respiratory syndrome (MERS) virus, examples of the enzyme inhibitors include inhibitors for hemagglutinin-esterase (HE) on the surface of the virus (HE antibody, 3,4-dichloroisocoumarin, 9-O-acetylated polysialoside or the like).

For example, when the pathogenic microorganism of interest is human immunodeficiency virus (HIV), hepatitis B virus, or human T cell leukemia virus (HTLV), examples of the enzyme inhibitors include inhibitors for reverse transcriptase on the surface of the virus or in the virus (RETROVIR (GlaxoSmithKline K.K., zidovudine/AZT), VIDEX (Bristol-Myers Squibb Inc., didanosine/ddI), HMD (Hoffmann-La Roche) (zalcitabine/ddC), ZERIT (Bristol-Myers Squibb, stavudine/d4T), EPIVIR (GlaxoSmithKline K.K, lamivudine/3TC), COMBIVIR (GlaxoSmithKline K.K., zidovudine/lamivudine), VIRAMUNE (Boehringer Ingelheim Pharmaceuticals Inc., nevirapine), RESCRIPTOR (Pharmacia/Upjohn, delavirdine), SUSTIVA (Dupont Pharma, Inc., efavirenz), and the like).

Similarly, for example, when the pathogenic microorganism of interest is Ebola virus, hepatitis C virus, Lassa virus, hantavirus, rabies virus, Japanese encephalitis virus, yellow fever virus, dengue virus, rubella virus, rotavirus, or norovirus, examples of the enzyme inhibitors include inhibitors for RNA-dependent RNA polymerase on the surface of the virus or in the virus (favipiravir, ribavirin or the like).

Furthermore, for example, when the pathogenic microorganism of interest is coliform group, *vibrio parahaemolyticus, campylobacter, enterobacter*, or *bacillus*, examples of the enzyme inhibitors include inhibitors for galactosidase on the surface of the bacterium or in the bacterium (Castanospermine, Conduritol B Epoxide, Bromoconduritol, 2-Deoxy-D-Galactose or the like), inhibitors for glucuronidase (Aceglatone, D-glucaro-1,4-lactone, lysophospholipid or the like), inhibitors for chymotrypsin and trypsin (trypsin inhibitors derived from a soybean and a chicken egg or the like, $Arg^4$-$Met^5$-marinostatin, Phenylmethylsulfonyl fluoride, Aminoethyl benzylsulfonyl fluoride, Aprotinin, Tosyl lysine chloromethyl ketone, tosyl phenylalanine chloromethyl ketone or the like), inhibitors for xylosidase (Castanospermine, Xyl-amidine or the like).

Thus, in the method for detecting the drug susceptibility of the pathogenic microorganism according to the present invention, the inhibitor may be appropriately selected by the enzyme present on the surface of the pathogenic microorganism of interest or in the pathogenic microorganism.

4. Method for Screening Anti-Pathogenic Microbial Agent

A method for screening an anti-pathogenic microbial agent according to the present invention includes the following steps:

(C1) an introducing step of introducing a hydrophilic solvent that contains a pathogenic microorganism, a substance serving as a substrate for a reaction involving an enzyme present on a surface of the pathogenic microorganism or in the pathogenic microorganism, and a candidate compound into a space between a lower-layer section in which a plurality of receptacles capable of storing the pathogenic microorganism are formed separately from each other by a side wall having a hydrophobic upper surface and an upper-layer section facing a side of the lower-layer section in which side the receptacles are formed;

(C2) an enclosing step of introducing a hydrophobic solvent into the space to form in the receptacle a droplet of the hydrophilic solvent that is covered with the hydrophobic solvent and envelopes the pathogenic microorganism, the substance, and the candidate compound; and (C3) a detecting step of optically detecting a reaction product produced by the reaction between the enzyme and the substance in the droplet (herein, the case where detection intensity of the reaction product in the presence of the candidate compound is less than detection intensity of the reaction product in the absence of the candidate compound indicates that the candidate compound has anti-pathogenic microorganism activity).

[Introducing Step (C1)]

The introducing step (C1) of the method for screening the anti-pathogenic microbial agent according to the present invention is different from the introducing step (A1) of the pathogenic microorganism detecting method only in that the candidate compound to be evaluated for the anti-pathogenic microorganism activity is contained in the hydrophilic solvent. In the introducing step (C1), in addition to the pathogenic microorganism and the substrate, the candidate compound enters the receptacles.

[Enclosing Step (C2)]

The operation of the enclosing step (C2) of the method for screening the anti-pathogenic microbial agent according to the present invention is the same as that of the enclosing step (A2) of the pathogenic microorganism detecting method. In the enclosing step (C2), the droplet of the hydrophilic solvent covered with the hydrophobic solvent and enveloping the pathogenic microorganism, the substrate, and the candidate compound is formed in the receptacles.

[Detecting Step (C3)]

In the detecting step (C3) of the method for screening the anti-pathogenic microbial agent according to the present invention, the reaction product produced in the droplet of the hydrophilic solvent is optically detected in the same manner as in the detecting step (A3) of the pathogenic microorganism detecting method.

The case where the detection intensity of the reaction product in the presence of the candidate compound is reduced as compared to the detection intensity of the reaction product in the absence of the candidate compound indicates that the production of the reaction product in the droplet of the hydrophilic solvent is suppressed by the candidate compound. That is, the enzyme contained in the pathogenic microorganism is inhibited, which indicates that the candidate compound has anti-pathogenic microorganism activity.

Meanwhile, the case where the detection intensity of the reaction product in the presence of the candidate compound is comparable with the detection intensity of the reaction product in the absence of the candidate compound indicates that the production of the reaction product in the droplet of the hydrophilic solvent is not suppressed by the inhibitor. That is, the enzyme contained in the pathogenic microorganism is not inhibited, which indicates that the candidate compound has no anti-pathogenic microorganism activity.

5. Pathogenic Microorganism Detection Kit

A kit according to the present invention is a kit for detecting a pathogenic microorganism in a biological sample separated from a subject infected with the pathogenic microorganism or a subject suspected to be infected with the pathogenic microorganism, the kit including:
an array including a lower-layer section in which a plurality of receptacles capable of storing the pathogenic microorganism are formed separately from each other by a side wall having a hydrophobic upper surface and an upper-layer section facing a side of the lower-layer section in which side the receptacles are formed, with a space between the lower-layer section and the upper-layer section;
a substance serving as a substrate for a reaction involving an enzyme present on a particle surface of the pathogenic microorganism or in the pathogenic microorganism;
a hydrophilic solvent containing at least one of a buffering substance or TMAO; and
a hydrophobic solvent.

The kit according to the present invention includes the array 1, the substrate 3, the hydrophilic solvent 42, and the hydrophobic solvent 43. The substrate 3, the hydrophilic solvent 42, and the hydrophobic solvent 43 have already been described above, and the constitution of the array 1 will be described below in more detail.

The lower-layer section 10 of the array 1 includes a plate-like member 11 and the side wall 12 having a hydrophobic upper surface. In the lower-layer section 10, the plurality of receptacles 13 are formed separately from each other by the side wall 12.

The plate-like member 11 preferably has a hydrophilic surface. The term "hydrophilic surface" refers to a surface whose affinity with a hydrophilic solvent is higher than affinity with a hydrophobic solvent. The plate-like member 11 only needs to be made of a solid material. For example, the plate-like member 11 can be made of glass, silicon, or a polymer resin.

The side wall 12 is a structure that is provided on a surface of the plate-like member 11, preferably on the hydrophilic surface of the plate-like member 11, and is configured to separate the plurality of receptacles 13 from each other. The side wall 12 has the hydrophobic upper surface. The term "hydrophobic" herein is used as a synonym for "lipophilic", and denotes a nature whose affinity with a hydrophobic solvent is higher than affinity with a hydrophilic solvent.

The side wall 12 is configured such that its upper surface, i.e., its surface facing the upper-layer section 20, is hydrophobic. A lateral surface of the side wall 12, i.e., an inner wall of each of the receptacles 13, may be either hydrophobic or hydrophilic.

For example, the side wall 12 may include a hydrophilic structure and a hydrophobic layer formed on an upper surface of the hydrophilic structure. The hydrophilic structure may be made of, for example, glass, silicon, or a polymer resin. The hydrophobic layer may be made of, for example, a water repellent resin or a fluorinated polymer resin. Examples of the fluorinated polymer resin include an amorphous fluorine resin. The amorphous fluorine resin is preferably used, because the amorphous fluorine resin has a high hydrophobic property and has a low toxicity to a biological sample.

As the amorphous fluorine resin, at least one selected from CYTOP®, TEFLON® AF2400, and TEFLON® AF1600 can be suitably used. Among these, CYTOP® is most preferable, since it is easy to be microfabricated.

For example, the side wall 12 may be made of a hydrophobic material. For example, the side wall 12 may be made of a fluorinated polymer resin or a paraxylene polymer resin. Examples of the fluorinated polymer resin include an amorphous fluorine resin. Any of the resins can be suitably used as the amorphous fluorine resin.

The side wall 12 has such a configuration that the plurality of receptacles 13 are formed on the plate-like member 11. For example, a plate-like structure having holes formed at positions at which the receptacles 13 are formed may be used for the side walls 12.

Each of the receptacles 13 has a bottom surface that is a part of the surface of the plate-like member 11, and the bottom surface is hydrophilic. A region surrounded by the bottom surface and the lateral surface of each of the receptacles 13 may be shaped in, for example, a circular cylinder or a rectangular column.

In the present embodiment, each of the receptacles 13 has the hydrophilic bottom surface, and the side wall 12 has the hydrophobic upper surface. This makes it possible to efficiently introduce the hydrophilic solvent 42 into the receptacles 13 in the introducing step (1), and to prevent the hydrophobic solvent 43 from entering the receptacles 13 in the enclosing step (2).

The upper-layer section 20 may be made of, for example, glass, silicon, or a polymer resin. The upper-layer section 20 faces the side of the lower-layer section 10 in which side the receptacles 13 are formed, with the space 30 between the lower-layer section 10 and the upper-layer section 20. That is, the space 30 exists between the side wall 12 and a hydrophobic layer 22. The space 30 serves as a flow path. Thus, the array 1 has a flow cell structure.

The space 30 can be used as the flow path for allowing a fluid to flow between the lower-layer section 10 and the upper-layer section 20 in a direction in parallel with the surfaces of the lower-layer section 10 and the upper-layer section 20, the surfaces of the lower-layer section 10 and the upper-layer section 20 facing each other.

The lower-layer section 10 or the upper-layer section 20 may be provided with the through-hole (not shown) through which the fluid is introduced into the space 30. For example, the lower-layer section 10 may have a region in which the receptacles 13 is formed and a region in which no receptacles 13 is formed. The lower-layer section 10 may have the through-hole in the region in which no receptacles 13 is formed; alternatively, the upper-layer section 20 may have the through-hole in a region facing the region of the lower-layer section 10 in which no receptacles 13 is formed.

In the present embodiment, the upper-layer section 20, which defines the top of the space 30 has a hydrophobic surface, and the bottom of the space 30 corresponds to the hydrophobic upper surface of the side wall 12 and the receptacles 13. Thus, except for portions of the space 30 corresponding to the bottom surfaces of the receptacles 13, the entire space 30 has a hydrophobic property. This makes it possible to efficiently introduce the hydrophilic solvent 42 into each of the receptacles 13 in the introducing step (1). This prevents the hydrophobic solvent 43 from entering each of the receptacles 13 in the enclosing step (2). Thus, by introducing the hydrophobic solvent 43 into the space 30, it is possible to efficiently form a droplet in each of the receptacles 13.

EXAMPLES

Test Example 1: Studying of pH Value of Hydrophilic Solvent

According to the following procedure, the influence of the pH value of a hydrophilic solvent on detection sensitivity was studied.

First, according to a report by Kim et al. ("Quantifying genetically inserted fluorescent protein in single iPS cells to monitor Nanog expression using electroactive microchamber arrays", Lab on Chip, 2014, Issue 4, Vol. 14, and p. 730-736), a droplet array device (DAD) was produced. A cover glass (24 mm×32 mm) was washed and dried. The cover glass was then spin-coated with an amorphous fluorine resin (CYTOP 816AP, AGC Inc.), and fired at 180° C. for 1 hour. The cover glass coated with the amorphous fluorine resin was spin-coated with a positive type photoresist (AZ-4903, AZ Electronic Materials), fired at 55° C. for 3 minutes, and then further fired at 110° C. for 5 minutes. The cover glass was subjected to photolithography by use of a photomask having holes each having a diameter of 3 µm at intervals of 5 µm. The cover glass was dry-etched with oxygen plasma, and then washed to obtain as the DAD. The DAD had wells (receptacles) each having a diameter of 4 µm and a depth of 3 µm (about $1,000,000/10$ $mm^2$), and the cover glass was exposed from the bottom surfaces of the wells. An array having a flow cell structure as shown in FIG. 1 was produced by use of the obtained DAD.

4-MU was dissolved in a concentration of 50 µM in a buffer solution (33 mM DEA-HCl, 4 mM $CaCl_2$) adjusted to a pH of 6.5 to 9.0.

Into the array, 30 µL of the buffer solution in which 4-MU was dissolved was introduced, to fill each of the wells with the buffer solution (see FIG. 1A). Then, into the array, 200 µL of a hydrophobic solvent (FC40) was introduced, to form a droplet of the hydrophilic solvent (buffer solution) covered with the hydrophobic solvent in each of the wells.

With a CMOS camera (Neo sCMOS, Andor) connected to a fluorescence microscope (IX8, OLYMPUS), a fluorescent image of each of the droplets was photographed to measure fluorescence intensity. A region of 10 $mm^2$ of each of the wells were divided into 120 parts, and photographed. One image includes about 8,600 wells. The fluorescent image was analyzed with an imaging analysis software (Meta-Morph, Molecular Devices), to calculate fluorescence intensity.

Figure 3:
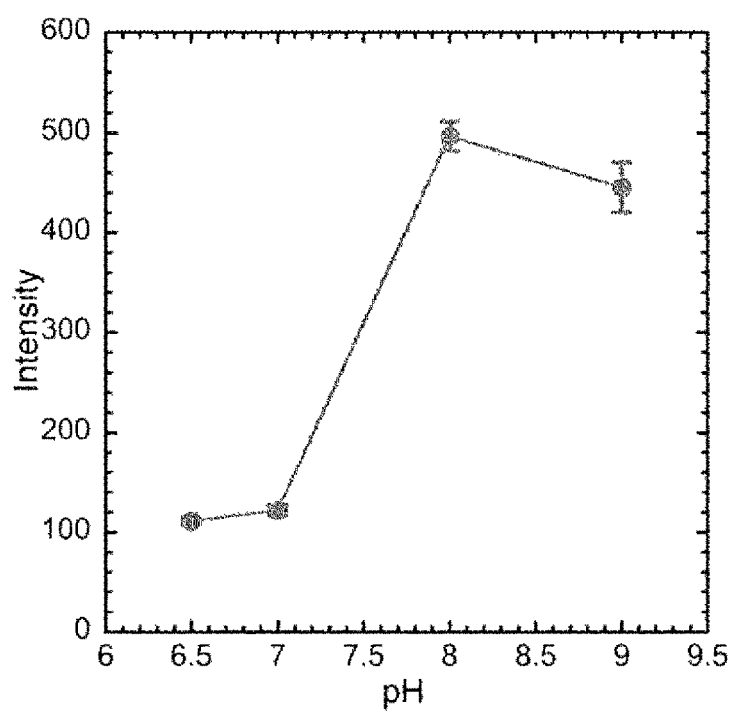
FIG. 3 is a graph showing a result of studying the influence of the pH of a hydrophilic solvent on detection sensitivity (Test Example 1).

The results are shown in FIG. 3. The fluorescence of 4 MU could be detected with higher sensitivity by setting the pH value of the buffer solution higher than the pKa (7.79) of 4 MU. This is considered to be because, in the pH value of 8 or more, 4 MU has a charge, whereby the distribution (leakage) of 4 MU to FC40 is suppressed.

Test Example 2: Studying 1 of Concentration of Buffering Substance of Hydrophilic Solvent According to the following procedure, the influence of the concentration of a buffering substance of a hydrophilic solvent on detection sensitivity was studied.

4-MU was dissolved in a concentration of 50 µM in a buffer solution (4 mM $CaCl_2$), pH 6.5) having a DEA concentration adjusted to 25 mM to 1 M.

Into the array, 30 µL of the buffer solution in which 4-MU was dissolved was introduced, to fill each of the wells with the buffer solution (see FIG. 1A). Then, into the array, 200 µL of a hydrophobic solvent (FC40) was introduced, to form a droplet of the hydrophilic solvent covered with the hydrophobic solvent (buffer solution) in each of the wells.

Time-lapse photographing was performed under a fluorescence microscope to measure fluorescence intensity of each of the droplets.

Figure 4:
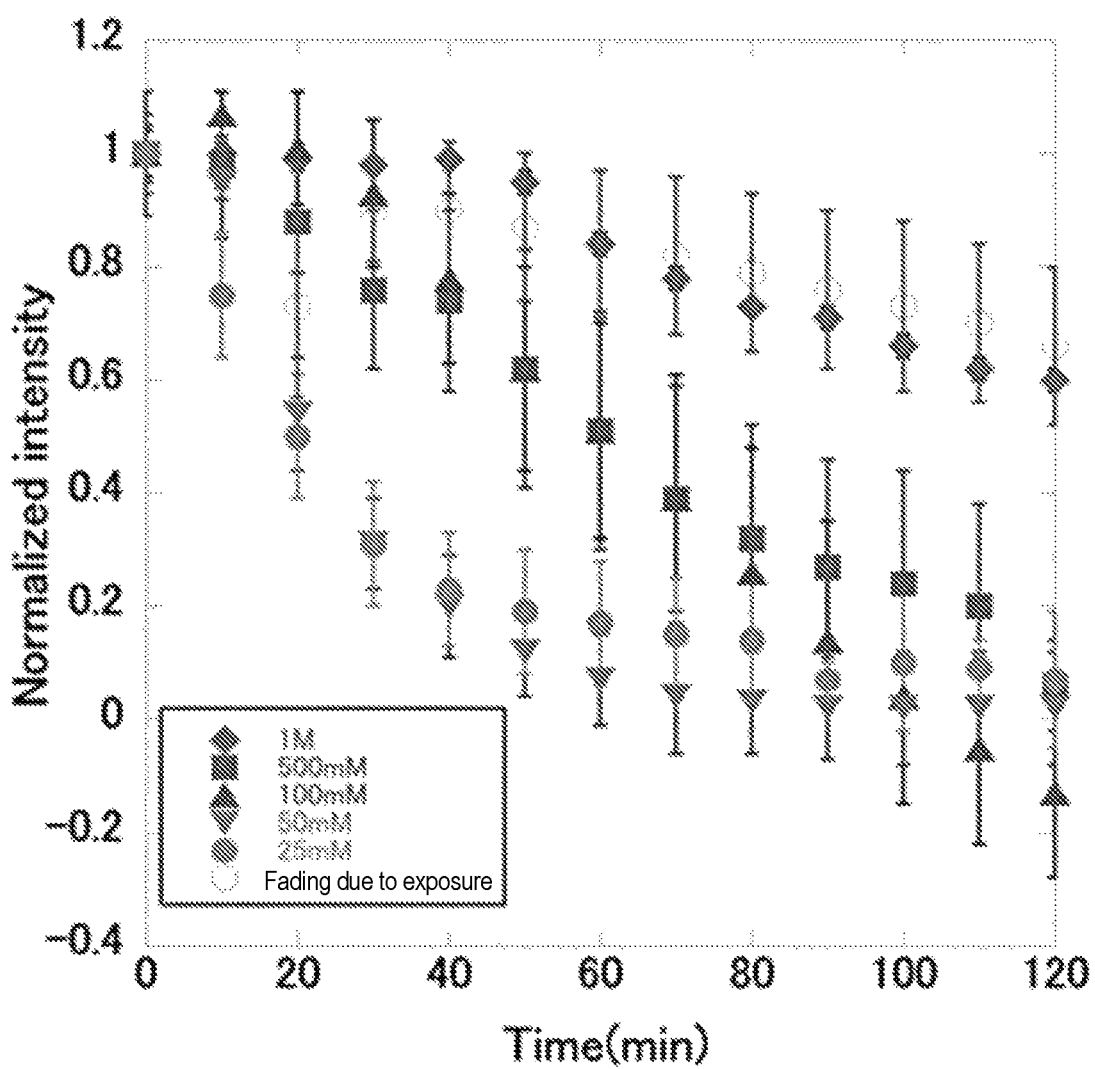
FIG. 4 is a graph showing a result of studying the influence of the concentration of a buffering substance (DEA) of a hydrophilic solvent on detection sensitivity (Test Example 2).

The results are shown in FIG. 4. In the graph, the horizontal axis represents a time after a droplet is formed, and the vertical axis represents the fluorescence intensity of the droplet as a relative value with intensity at time 0 taken as 1. In the DEA concentration of 1 M, the decrease in the fluorescence intensity over time was not observed after subtraction of the influence of fading due to exposure. Also in the DEA concentrations of 500 mM and 100 mM, the decrease in the fluorescence intensity was suppressed for 30 minutes after the observation.

Considering that a time required for the detection is about several minutes in the detecting method according to the present invention, the fluorescence of 4 MU was shown to be detectable with higher sensitivity by setting the concentration of the buffering substance in the buffer solution to 100 mM or more, preferably 500 mM or more, and more preferably 1 M or more. The distribution (leakage) of 4 MU to FC40 was suppressed by adding the buffering substance in a concentration equal to or greater than a predetermined concentration into the buffer solution.

Test Example 3: Studying 2 of Concentration of Buffering Substance of Hydrophilic Solvent A test was performed in the same manner as in Test Example 2 except that the buffering substance was changed to HEPES (concentration: 1 M or 100 mM, pH: 8.0) from DEA, and the concentration of 4-MU was set to 200 µM.

Figure 5:
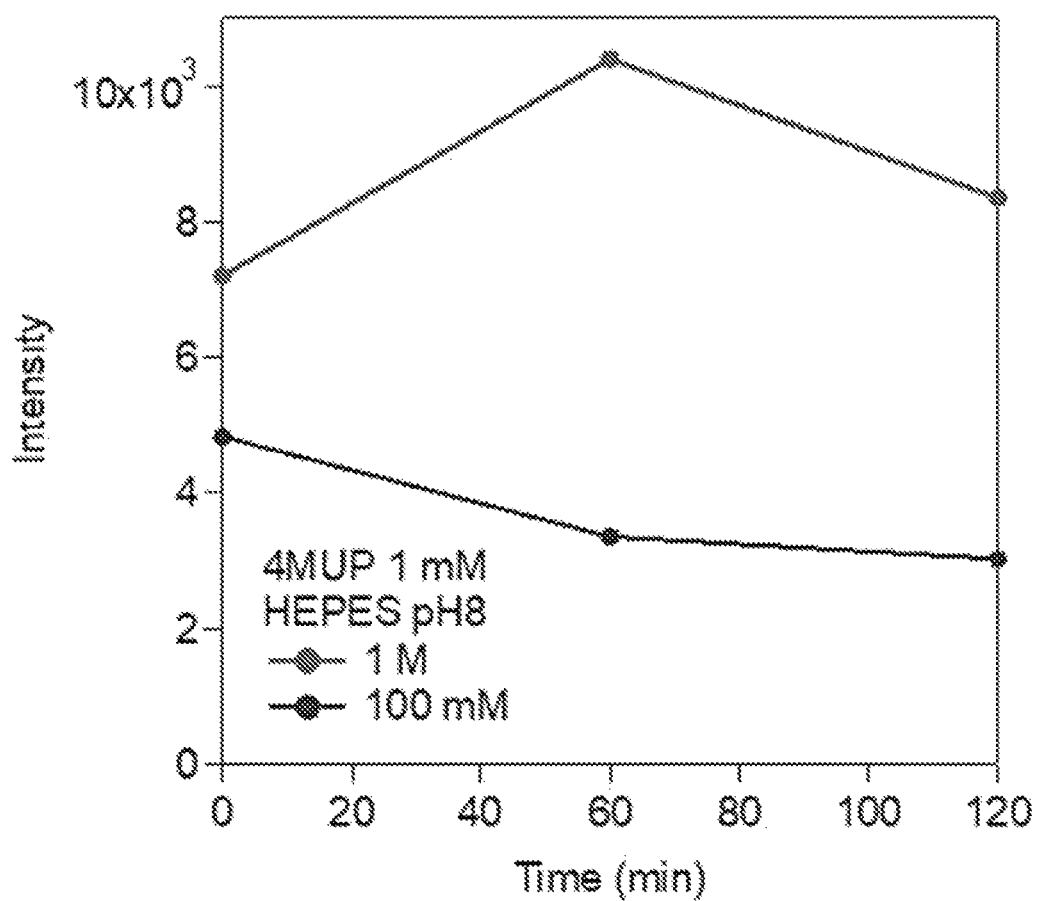
FIG. 5 is a graph showing a result of studying the influence of the concentration of a buffering substance (HEPES) of a hydrophilic solvent on detection sensitivity (Test Example 3).

The results are shown in FIG. 5. In the graph, the horizontal axis represents a time after a droplet is formed, and the vertical axis represents the fluorescence intensity of the droplet. In the HEPES concentration of 1 M, the decrease in the fluorescence intensity over time was not observed. The distribution (leakage) of 4 MU to FC40 was suppressed by adding the buffering substance in a concentration equal to or greater than a predetermined concentration into the buffer solution.

Test Example 4: Studying of Trimethylamine Oxide

According to the following procedure, the influence of the concentration of TMAO of a hydrophilic solvent on detection sensitivity was studied.

4-MU or fluorescein was dissolved in a concentration of 200 µM in a buffer solution (4 mM $CaCl_2$, pH 9.0) having a DEA concentration adjusted to 1 mM or 1 M. TMAO having a concentration of 1 M was added into the buffer solution having a DEA concentration adjusted to 1 mM, and 4-MU or fluorescein was dissolved in a concentration of 200 µM.

Into the array, 30 µL of the buffer solution in which 4-MU or fluorescein was dissolved was introduced, to fill each of the wells with the buffer solution (see FIG. 1A). Then, into the array, 200 µL of a hydrophobic solvent (FC40) was introduced, to form a droplet of the hydrophilic solvent (buffer solution) covered with the hydrophobic solvent in each of the wells.

Time-lapse photographing was performed under a fluorescence microscope to measure fluorescence intensity of each of the droplets.

Figure 6:
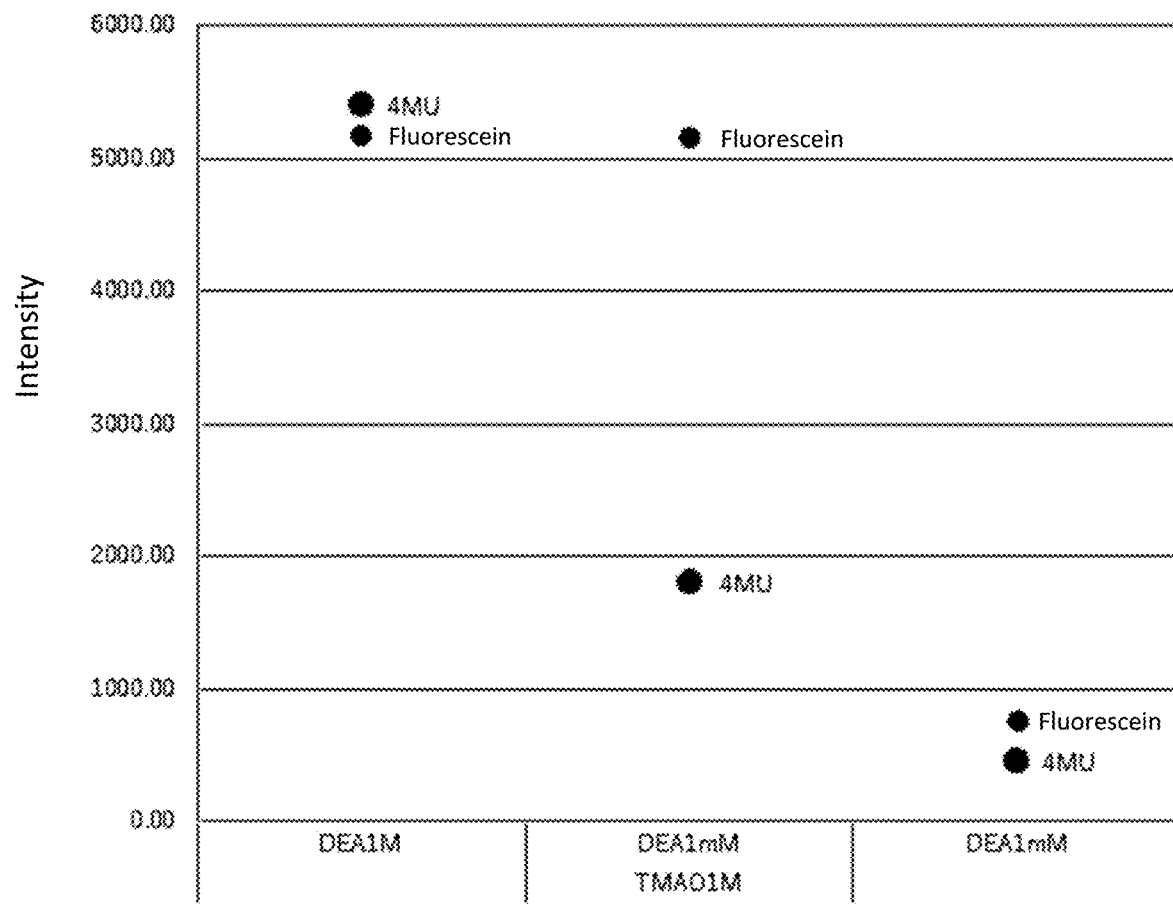
FIG. 6 is a graph showing a result of studying the influence of the concentration of TMAO of a hydrophilic solvent on detection sensitivity (Test Example 4).

The results are shown in FIG. 6. The graph represents the fluorescence intensity of a droplet for 60 minutes after the droplet is formed. The decrease in the fluorescence intensity was not observed under the condition of the DEA concentration of 1 M, and the effect of suppressing the distribution (leakage) of 4 MU and fluorescein to FC40 was observed. However, the effect was not observed under the condition of the DEA concentration of 1 mM. This result coincides with the result of Test Example 2.

On the other hand, under the condition that TMAO of 1 M was added to a buffer solution having a DEA concentration of 1 mM, the effect of suppressing the distribution (leakage) of 4 MU and fluorescein to FC40 was observed. In particular, the effect was remarkable in fluorescein.

By adding TMAO in a concentration equal to or greater than a predetermined concentration into the buffer solution, the distribution (leakage) of 4 MU and fluorescein to FC40 was suppressed.

Test Example 5: Studying 3 of Concentration of Buffering Substance of Hydrophilic Solvent According to the following procedure, the influence of the concentration of glycine or sarcosine in a hydrophilic solvent on detection sensitivity was studied.

4-MU (200 µM) and glycine (1 M or 2.7 M) or sarcosine (1 M or 4.5 M) were dissolved in the buffer solution (4 mM $CaCl_2$, pH 9.0) having a DEA concentration adjusted to 1 mM. As a reference, a buffer solution into which glycine and sarcosine were not added was used.

A droplet of the hydrophilic solvent (buffer solution) covered with the hydrophobic solvent in each of wells of an array was formed in the same manner as in Test Example 4.

Time-lapse photographing was performed under a fluorescence microscope to measure fluorescence intensity of each of the droplets.

Figure 7:
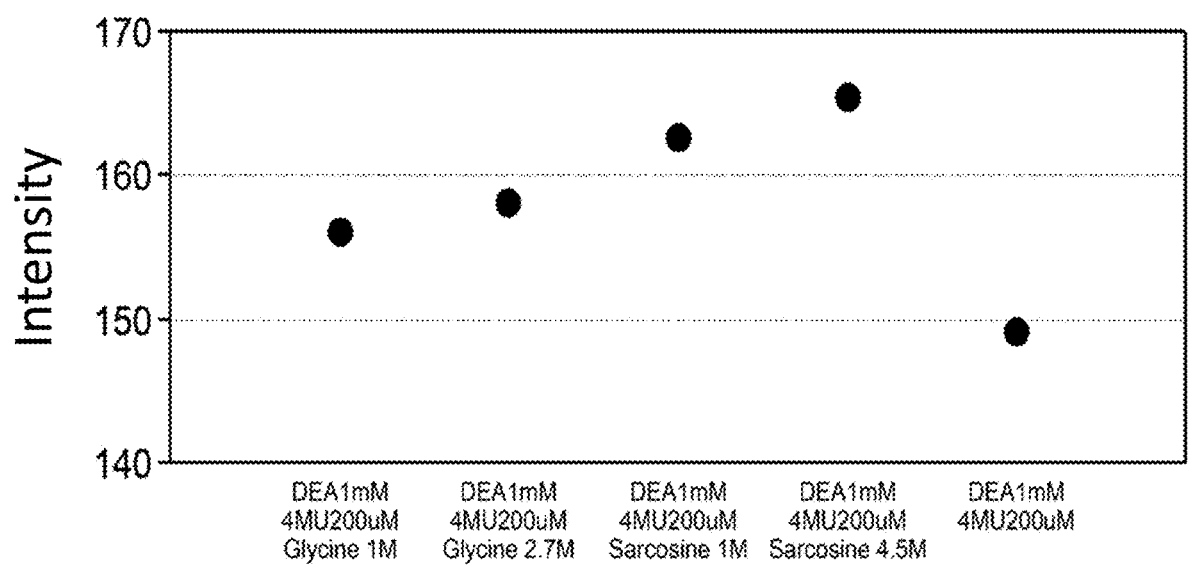
FIG. 7 is a graph showing a result of studying the influence of the concentration of a buffering substance (sarcosine or glycine) of a hydrophilic solvent on detection sensitivity (Test Example 5).

The results are shown in FIG. 7. The graph represents the fluorescence intensity of a droplet for 60 minutes after the droplet is formed. Under the condition that glycine and sarcosine were added, the decrease in the fluorescence intensity was suppressed as compared with a case under the condition that glycine and sarcosine were not added, and the effect of suppressing the distribution (leakage) of 4 MU to FC40 was observed.

The distribution (leakage) of 4 MU to FC40 was suppressed by adding the buffering substance in a concentration equal to or greater than a predetermined concentration into the buffer solution.

REFERENCE SIGNS LIST

1: array, 2: virus, 3: substrate, 4: reaction product, 5: enzyme, 10: lower-layer section, 11: plate-like member, 12: side wall, 13: receptacle, 20: upper-layer section, 30: space, 42: hydrophilic solvent, 43: hydrophobic solvent

The invention claimed is:

1. A method for detecting a reaction product, comprising reacting an enzyme with a substance serving as a substrate for a reaction involving the enzyme in a hydrophilic solvent that is in interfacial contact with a hydrophobic solvent, wherein the reaction product is produced directly and released from the substrate, and
   wherein the hydrophilic solvent contains at least one of a buffering substance or trimethylamine oxide (TMAO), and wherein the concentration of the buffering substance in the hydrophilic solvent is at least 500 mM.

2. The method according to claim 1, wherein the concentrations of the buffering substance and trimethylamine oxide in the hydrophilic solvent are at least 1 M.

3. The method according to claim 1, wherein the buffering substance is selected from the group of consisting of DEA (diethanolamine), HEPES (4-(2-hydroxyethyl)-1-piperazineethanesulfonic acid), glycine, and sarcosine.

4. The method according to claim 1, wherein the hydrophilic solvent has a pH value greater than an acid dissociation constant (pKa) of the reaction product.

5. The method according to claim 1,
   wherein:
   the hydrophilic solvent contains a pathogenic microorganism;
   the enzyme is an enzyme present on a surface of the pathogenic microorganism or in the pathogenic microorganism and having substrate cleavage activity;
   the substance is a chromogenic substrate; and
   the reaction product produced by cleavage of the chromogenic substrate involving the enzyme is optically detected.

6. The method according to claim 5,
   wherein:
   the pathogenic microorganism is influenza virus;
   the enzyme is neuraminidase; and the chromogenic substrate and the reaction product are 4-methylumbelliferyl-N-acetyl-α-D-neuraminic acid and 4-methylumbelliferone, respectively, or a derivative containing fluorescein and fluorescein, respectively.

7. The method according to claim 5, wherein the hydrophilic solvent contains a biological sample separated from a subject infected with the pathogenic microorganism or a subject suspected to be infected with the pathogenic microorganism.

8. A method for detecting a reaction product, comprising reacting an enzyme with a substance serving as a substrate for a reaction involving the enzyme in a hydrophilic solvent that is in interfacial contact with a hydrophobic solvent, wherein the reaction product is produced directly and released from the substrate,
the method comprising:
a step of adding at least one of a buffering substance or trimethylamine oxide (TMAO) to the hydrophilic solvent to suppress migration of the reaction product to the hydrophobic solvent from the hydrophilic solvent, wherein the concentration of the buffering substance in the hydrophilic solvent is at least 500 mM.

9. The method according to claim 2, wherein the buffering substance is selected from the group of consisting of DEA (diethanolamine), of HEPES (4-(2-hydroxyethyl)-1-piperazineethanesulfonic acid), glycine, and sarcosine.

10. The method according to claim 6,
wherein the hydrophilic solvent contains a biological sample separated from a subject infected with the pathogenic microorganism or a subject suspected to be infected with the pathogenic microorganism.

11. The method according to claim 8, wherein the concentrations of the buffering substance and trimethylamine oxide in the hydrophilic solvent are at least 1 M.

12. The method according to claim 1, wherein the buffering substance is DEA (diethanolamine).

13. The method according to claim 1, wherein the buffering substance is glycine.

14. The method according to claim 1, wherein the buffering substance is sarcosine.

15. The method according to claim 1, wherein the hydrophilic solvent contains trimethylamine oxide (TMAO).

* * * * *